(12) United States Patent
Mirkin et al.

(10) Patent No.: US 9,617,541 B2
(45) Date of Patent: Apr. 11, 2017

(54) BIOCOMPATIBLE INFINITE COORDINATION POLYMER NANOPARTICLE-NUCLEIC ACID CONJUGATES FOR ANTISENSE GENE REGULATION

(71) Applicant: NORTHWESTERN UNIVERSITY, Evanston, IL (US)

(72) Inventors: Chad A. Mirkin, Wilmette, IL (US); Colin Michael Calabrese, Evanston, IL (US); William E. Briley, Chicago, IL (US); Timothy J. Merkel, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/831,316

(22) Filed: Aug. 20, 2015

(65) Prior Publication Data

US 2016/0053260 A1 Feb. 25, 2016

Related U.S. Application Data

(60) Provisional application No. 62/039,696, filed on Aug. 20, 2014.

(51) Int. Cl.
| | | |
|---|---|---|
| C12Q 1/68 | (2006.01) |
| C12N 15/113 | (2010.01) |
| C07D 213/69 | (2006.01) |
| C07F 15/02 | (2006.01) |
| C12N 15/11 | (2006.01) |
| B82Y 5/00 | (2011.01) |
| B82Y 15/00 | (2011.01) |

(52) U.S. Cl.
CPC .......... *C12N 15/113* (2013.01); *C07D 213/69* (2013.01); *C07F 15/02* (2013.01); *C12N 15/111* (2013.01); *B82Y 5/00* (2013.01); *B82Y 15/00* (2013.01); *C12N 2310/11* (2013.01); *C12N 2310/14* (2013.01); *C12N 2310/351* (2013.01); *C12N 2310/51* (2013.01); *C12N 2320/32* (2013.01)

(58) Field of Classification Search
CPC .................................................... C12N 15/113
USPC ......................................................... 435/6.1
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh Dinh et al. |
| 5,130,302 A | 7/1992 | Spielvogel et al. |
| 5,134,066 A | 7/1992 | Rogers et al. |

(Continued)

FOREIGN PATENT DOCUMENTS

| | | |
|---|---|---|
| EP | 1072679 A2 | 1/2001 |
| WO | WO-97/12896 A1 | 4/1997 |

(Continued)

OTHER PUBLICATIONS

Alkilany et al., Toxicity and cellular uptake of gold nanoparticles: what we have learned so far?, J. Nanoparticle Res., 12(7):2313-33 (2010).

(Continued)

*Primary Examiner* — Jezia Riley
(74) *Attorney, Agent, or Firm* — Marshall, Gerstein & Borun LLP

(57) ABSTRACT

Disclosed herein are metal-ligand complexes containing polynucleotides, compounds for making the same, and methods of using the same.

16 Claims, 5 Drawing Sheets

(56) References Cited

U.S. PATENT DOCUMENTS

| | | | |
|---|---|---|---|
| 5,175,273 | A | 12/1992 | Bischofberger et al. |
| 5,270,163 | A | 12/1993 | Gold et al. |
| 5,367,066 | A | 11/1994 | Urdea et al. |
| 5,432,272 | A | 7/1995 | Benner |
| 5,457,187 | A | 10/1995 | Gmeiner et al. |
| 5,459,255 | A | 10/1995 | Cook et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,552,540 | A | 9/1996 | Haralambidis |
| 5,587,469 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,637,459 | A | 6/1997 | Burke et al. |
| 5,645,985 | A | 7/1997 | Froehler et al. |
| 5,681,941 | A | 10/1997 | Cook et al. |
| 5,750,692 | A | 5/1998 | Cook et al. |
| 5,763,588 | A | 6/1998 | Matteucci et al. |
| 5,830,653 | A | 11/1998 | Froehler et al. |
| 6,005,096 | A | 12/1999 | Matteucci et al. |
| 7,223,833 | B1 | 5/2007 | Nielsen et al. |

FOREIGN PATENT DOCUMENTS

| | | |
|---|---|---|
| WO | WO-2007/047455 A2 | 4/2007 |
| WO | WO-2008/151049 A2 | 12/2008 |

OTHER PUBLICATIONS

Altschul et al., Basic local alignment search tool, J. Mol. Biol., 215(3):403-10 (1990).

Burgess et al., Hydroxypyranones, hydroxypyridinones, and their complexes, Adv. Inorg. Chem., 60:167-243 (2008).

Calabrese et al., Biocompatible infinite-coordination-polymer nanoparticle-nucleic-acid conjugates for antisense gene regulation, Angew. Chem. Int. Ed. Engl., 54(2):476-80 (2015).

Caulder et al., Design, formation and properties of tetrahedral M(4)L(4) and M(4)L(6) supramolecular clusters, J. Am. Chem. Soc., 123(37):8923-38 (2001).

Chien et al., DNA-nanoparticle micelles as supramolecular fluorogenic substrates enabling catalytic signal amplification and detection by DNAzyme probes, Chem. Commun. (Camb.): 47(1):167-9 (2011).

Cho et al., [Bis(catechol)salen]MnIII Coordination Polymers as Support-Free Heterogeneous Asymmetric Catalysts for Epoxidation, Eur. J. Inorg. Chem., 31:4863-7 (2007).

Choi et al., Mechanism for the endocytosis of spherical nucleic acid nanoparticle conjugates, Proc. Natl. Acad. Sci. USA, 110(19):7625-30 (2013).

Cook, Anti-Cancer Drug Design, Concise Encyclopedia of Polymer Science and Engineering, John Wiley & Sons, 6:585-607 (1991).

Crawford et al., Peptide aptamers: Tools for biology and drug discovery. 2(1): 72-9 (2003).

Cutler et al., Polyvalent nucleic acid nanostructures, J. Am. Chem. Soc., 133(24):9254-7 (2011).

Cutler et al., Polyvalent oligonucleotide iron oxide nanoparticle "click" conjugates, Nano Lett., 10(4):1477-80 (2010).

Cutler et al., Spherical nucleic acids, J. Am. Chem. Soc., 134(3):1376-91 (2012).

Dhar et al., Polyvalent oligonucleotide gold nanoparticle conjugates as delivery vehicles for platinum(IV) warheads, J. Am. Chem. Soc., 131(41):14652-3 (2009).

Dougan et al., Enhanced oligonucleotide-nanoparticle conjugate stability using thioctic acid modified oligonucleotides, Nucleic Acids Res., 35(11):3668-75 (2007).

Englisch et al., Chemically modified oligonucleotides as probes and inhibitors, *Ang. Chem. Int. Ed.,* 30:613-29 (1991).

Freier et al., The ups and downs of nucleic acid duplex stability: structure-stability studies on chemically-modified DNA:RNA duplexes, Nucleic Acids Res., 25:4429-43 (1997).

Gao et al., A new type of pH-responsive coordination polymer sphere as a vehicle for targeted anticancer drug delivery and sustained release, J. Mater. Chem. B, 1:3202-8 (2013).

Giljohann et al., Gene regulation with polyvalent siRNA-nanoparticle conjugates, J. Am. Chem. Soc., 131(6):2072-3 (2009).

Hurst et al., Maximizing DNA loading on a range of gold nanoparticle sizes, Anal. Chem., 78(24):8313-8 (2006).

Huxford et al., Lipid-coated nanoscale coordination polymers for targeted delivery of antifolates to cancer cells, Chem. Sci., 3:198-204 (2012).

International Search Report and Written Opinion, International Application No. PCT/US2015/046075, mailed Nov. 9, 2015.

Jensen et al., Spherical nucleic acid nanoparticle conjugates as an RNAi-based therapy for glioblastoma, Sci. Transl. Med., 5(209):209ra152 (2013).

Katz, The reversible reaction of sodium thymonucleate and mercuric chloride, J. Am. Chem. Soc., 74:2238-45 (1951).

Kopylov et al., Combinatorial chemistry of nucleic acids: SELEX, Mol. Biol., 34: 940-54 (2000).

Kosturko et al., The crystal and molecular structure of a 2:1 complex of 1-methylthymine-mercury(II), Biochemistry, 13:3949-52 (1974).

Kroschwitz (ed.), *The Concise Encyclopedia of Polymer Science and Engineering,* pp. 858-859, New York: John Wiley & Sons (1990).

Lee et al., Silver nanoparticle-oligonucleotide conjugates based on DNA with triple cyclic disulfide moieties, Nano Lett., 7(7):2112-5 (2007).

Li et al., Quantum dot-antisense oligonucleotide conjugates for multifunctional gene transfection, mRNA regulation, and tracking of biological processes, Biomaterials, 32(7):1923-31 (2011).

Li et al., Reversible and Chemically Programmable Micelle Assembly with DNA Block-Copolymer Amphiphiles, Nano Letters, 4(6):1055-8 (2004).

Lin et al., Modular synthesis of functional nanoscale coordination polymers, Angew. Chem. Int. Ed. Engl., 48(4):650-8 (2009).

Liu et al., Design of iron chelators with therapeutic application, Coord. Chem. Rev., 232(1-2):151-71 (2002).

Lytton-Jean et al., Five years of siRNA delivery: spotlight on gold nanoparticles, Small, 7(14):1932-7 (2011).

Macfarlane et al., Nanoparticle superlattice engineering with DNA, Science, 334(6053):204-8 (2011).

Mirkin et al., A DNA-based method for rationally assembling nanoparticles into macroscopic materials, Nature, 382(6592):607-9 (1996).

Nunes et al., Multifunctional iron-chelators with protective roles against neurodegenerative diseases, Dalton Trans., 42(17):6058-73 (2013).

Nuruchi et al., Potentiometric, spectrophotometric and calorimetric study on iron(III) and copper(II) complexes with 1,2-dimethyl-3-hydroxy-4-pyridinone, J. Inorg. Biochem., 102(4):684-92 (2008).

Nykypanchuk et al., DNA-guided crystallization of colloidal nanoparticles, Nature, 451(7178):549-52 (2008).

Patel et al., Scavenger receptors mediate cellular uptake of polyvalent oligonucleotide-functionalized gold nanoparticles, Bioconjug. Chem., 21(12):2250-6 (2010).

Prigodich et al., Multiplexed nanoflares: mRNA detection in live cells, Anal. Chem., 84(4):2062-6 (2012).

Rieter et al., Nanoscale coordination polymers for platinum-based anticancer drug delivery, J. Am. Chem. Soc., 130(35):11584-5 (2008).

Rosi et al., Oligonucleotide-modified gold nanoparticles for intracellular gene regulation, Science, 312:1027-30 (2006).

Rush et al., Intracellular mRNA regulation with self-assembled locked nucleic acid polymer nanoparticles, J. Am. Chem. Soc., 136(21):7615-8 (2014).

Rush et al., Nuclease-resistant DNA via high-density packing in polymeric micellar nanoparticle coronas, ACS Nano, 7(2):1379-87 (2013).

Sabet et al., Computer-aided design of novel antibacterial 3-hydroxypyridine-4-ones: application of QSAR methods based on the MOLMAP approach, J. Comput. Aided Mol. Des., 26(3):349-61 (2012).

(56) References Cited

OTHER PUBLICATIONS

Sanghvi, Heterocyclic base modifications in nucleic acids and their applications in antisense oligonucleotides, Chapter 15 in Crooke et al. (eds.), *Antisense Research and Applications,* CRC Press (1993).
Scarrow et al., Ferric ion sequestering agents. 13. Synthesis, structures, and thermodynamics of complexation of cobalt(III) and iron(III) tris complexes of several chelating hydroxypyridinones, Inorg. Chem., 24(6):954-67 (1985).
Seferos et al., Nano-Flares: Probes for Transfection and mRNA Detection in Living Cells, J. Am. Chem. Soc., 129(50):15477-9 (2007).
Spokoyny et al., Infinite coordination polymer nano- and microparticle structures, Chem. Soc. Rev., 38(5):1218-27 (2009).
Sun et al., DNA-functionalized quantum dots: fabrication, structural, and physicochemical properties, Langmuir, 29(23):7038-46 (2013).
Szigethy et al., Influence of linker geometry on uranyl complexation by rigidly linked bis(3-hydroxy-N-methyl-pyridin-2-one), Inorg. Chem., 49(14):6755-65 (2010).
Thomas, the interaction of HgCl2 with sodium thymonucleate, J. Am. Chem. Soc., 76:6032-4 (1954).
Thompson et al., Ultrasensitive DNA detection using oligonucleotide-silver nanoparticle conjugates, Anal. Chem., 80(8):2805-10 (2008).
Tuerk et al., Systematic evolution of ligands by exponential enrichment: RNA ligands to bacteriophage T4 DNA polymerase. Science, 249: 505-10 (1990).
Wagner et al., Synthesis of oligonucleotide-functionalized magnetic nanoparticles and study on their in vitro cell uptake, Appl. Organomet. Chem., 18:514-9 (2004).
Wei et al., Polyvalent immunostimulatory nanoagents with self-assembled CpG oligonucleotide-conjugated gold nanoparticles, Angew. Chem. Int. Ed. Engl., 51(5):1202-6 (2012).
Yamane et al., On the complexing of desoxyribonucleic acid (DNA) by mercuric ion, J. Am. Chem. Soc., 83:2599-607 (1961).
Yan et al., Aptamers and aptamer targeted delivery. RNA Biol., 6: 316-20 (2009).
Young et al., Hollow spherical nucleic acids for intracellular gene regulation based upon biocompatible silica shells, Nano Lett., 12(7):3867-71 (2012).
Zhang et al., An extremely stable and orthogonal DNA base pair with a simplified three-carbon backbone, J. Am. Chem. Soc., 127:74-5 (2005).
Zhang et al., Antibody-linked spherical nucleic acids for cellular targeting, J. Am. Chem. Soc., 134(40):16488-91 (2012).
Zhang et al., PowerBlast: A new network BLAST application for interactive or automated sequence analysis and annotation. Genome, 7: 649-56 (1997).
Zhang et al., Strategy for increasing drug solubility and efficacy through covalent attachment to polyvalent Dna-nanoparticle conjugates, ACS Nano, 5(9):6962-70 (2011).
Zheng et al., Aptamer nano-flares for molecular detection in living cells, Nano Lett., 9(9):3258-61 (2009).
Zimmerman et al., "A novel silver(I)-mediated DNA base pair," J. Am. Chem. Soc., 124:13684-13685 (2002).
Morris et al., Nucleic acid-metal organic framework (MOF) nanoparticle conjugates, 136(20):7261-4 (2014).
He et al., Nanoscale metal-organic frameworks for the co-delivery of cisplatin and pooled siRNAs to enhance therapeutic efficacy in drug-resistant ovarian cancer cells, J. Am. Chem. Soc., 136(14):5181-4 (2014).
Ciupa et al., Multicellular aggregation of maltol-modified cells triggered by Fe(3+) ions, Chem. Commun. (Camb), 49(86):10148-50 (2013).
Menyo et al., Versatile tuning of supramolecular hydrogels through metal complexation of oxidation-resistant catechol-inspired ligands, Soft Matter, 9:10314-23 (2013).

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
```

```
<223> OTHER INFORMATION: Synthetic polynucleotide
<220> FEATURE:
<221> NAME/KEY: misc_feature
<222> LOCATION: (1)..(1)
<223> OTHER INFORMATION: 5' DBCO-TEG

<400> SEQUENCE: 1
aaaaaatcct tatcaatatt t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5' DBCO-TEG

<400> SEQUENCE: 2
aaaaaatcct tatcaatatt t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Hexane thiol

<400> SEQUENCE: 3
aaaaaatcct tatcaatatt t                                              21

<210> SEQ ID NO 4
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5' DBCO

<400> SEQUENCE: 4
ctccatggtg ctcac                                                     15

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5' DBCO

<400> SEQUENCE: 5
ctccttcacc ttcgcgcagc                                                20

<210> SEQ ID NO 6
<211> LENGTH: 18
<212> TYPE: DNA
<213> ORGANISM: Artificial Sequence
```

```
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5' DBCO-TEG
<220> FEATURE:
<221> NAME/KEY: misc_feature
<222> LOCATION: (10)..(10)
<223> OTHER INFORMATION: n is Cy5

<400> SEQUENCE: 6
cctcctcctc ctcctcct                                                       18

<210> SEQ ID NO 7
<211> LENGTH: 19
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Hexane thiol
<220> FEATURE:
<221> NAME/KEY: misc_feature
<222> LOCATION: (10)..(10)
<223> OTHER INFORMATION: Cy5

<400> SEQUENCE: 7
cctcctcctn cctcctcct                                                      19

<210> SEQ ID NO 8
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is Cy5
<220> FEATURE:
<221> NAME/KEY: misc_feature
<222> LOCATION: (21)..(21)
<223> OTHER INFORMATION: Propane thiol

<400> SEQUENCE: 8 ntttttttttt tttttttttt t                                                  21
```

BIOCOMPATIBLE INFINITE COORDINATION POLYMER NANOPARTICLE-NUCLEIC ACID CONJUGATES FOR ANTISENSE GENE REGULATION

STATEMENT OF GOVERNMENT SUPPORT

This invention was made with government support under W911NF-11-1-0229 awarded by the Army Research Office; U54 CA151880 awarded by the National Institutes of Health; and HR0011-13-2-0018 awarded by the Defense Advanced Research Projects Agency (DARPA). The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "2014-110_Seqlisitng.txt," 2,619 bytes, created Aug. 20, 2015.

BACKGROUND

Spherical nucleic acids (SNAs) have emerged as an interesting new class of materials that have shown promise in programmable materials synthesis, bio-detection, and intracellular gene regulation. Such structures are often comprised of a nanoparticle core functionalized with a dense layer of oligonucleotides. The most heavily studied SNA constructs are composed of a gold core functionalized with alkylthiol-modified DNA. Although SNAs made from gold have shown commercial promise as medical diagnostic and research tools and have shown no acute toxicity in vivo,] there are concerns about the potential long term toxicity of gold nanoparticles and their metabolic fate. Consequently, new forms of SNAs that have cores made of biocompatible materials are highly sought after.

SUMMARY

Provided herein are compounds having a structure:

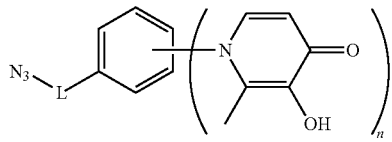

wherein L is $C_{1-20}$alkylene or —C(O)NH—$C_{1-20}$alkylene; and n is 1 or 2. In some cases, n is 1, and in specific cases, the pyridone is attached at the para position on the phenyl ring. In some cases, n is 2, and in specific cases, the pyridones are attached at each meta position on the phenyl ring. In various cases, L is $C_{1-20}$alkylene. In some cases, L is —C(O)NH—$C_{1-20}$alkylene.

Also provided herein is a metal-ligand complex comprising or a compound as disclosed herein and Fe(III). In some cases, the metal-ligand complex is in the form of an infinite coordination polymer (ICP) having a repeating formula of $Fe_2(Compound)_3$, or ratio of 3 Compound moieties for every 2 Fe(III) ions. In some cases, the metal-ligand complex further comprises a polynucleotide covalently attached via an alkyne moiety on the polynucleotide to the azide on one of the Compounds to form a triazole linkage. In some cases, the polynucleotide is attached to a surface azide on the ICP.

Further provided are polynucleotides comprising at a terminus a moiety comprising

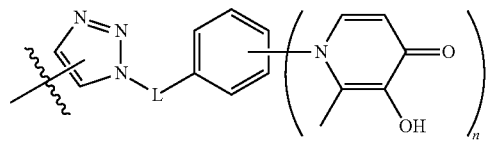

wherein L is $C_{1-20}$alkylene or —C(O)NH—$C_{1-20}$alkylene; and n is 1 or 2. In some cases, n is 1, and in specific cases, the pyridone is attached at the para position on the phenyl ring. In some cases, n is 2, and in specific cases, the pyridones are attached at each meta position on the phenyl ring. In various cases, L is $C_{1-20}$alkylene. In some cases, L is —C(O)NH—$C_{1-20}$alkylene. In some cases, the terminus of the polynucleotide has a structure

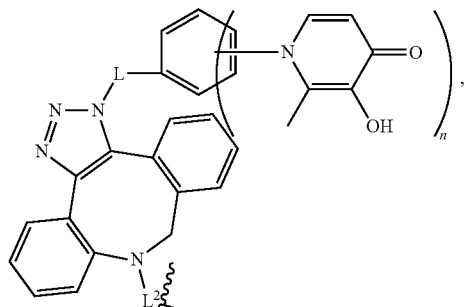

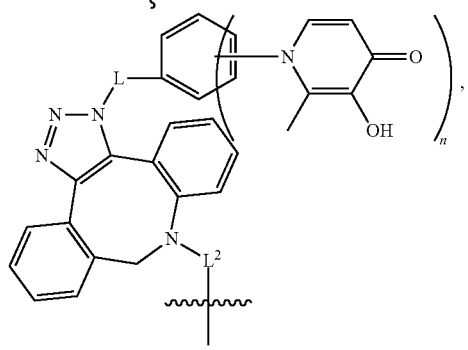

or a mixture thereof, $L^2$ is $C_{1-10}$ alkylene, —C(O)—$C_{1-10}$ alkylene-Y—, and —C(O)—$C_{1-10}$ alkylene-Y—$C_{1-10}$ alkylene-$(OCH_2CH_2)_m$—Y—; each Y is independently selected from the group consisting of a bond, C(O), O, NH, C(O)NH, and NHC(O); and m is 0, 1, 2, 3, 4, or 5. The polynucleotide can comprise DNA. The polynucleotide can comprise 5 to 100 nucleobases, or 10 to 60 nucleobases, or 15 to 30 nucleobases. Further provided herein is a metal-ligand complex comprising a polynucleotide as disclosed herein and Fe(III).

Further provided herein is a supramolecular structure comprising a first metal-ligand complex disclosed herein and a second metal-ligand complex disclosed herein, wherein the polynucleotide of the first metal-ligand complex is sufficiently complementary to the polynucleotide of the second metal-ligand complex to hybridize under appropriate conditions.

Also provided herein are methods of inhibiting expression of a gene product encoded by a target polynucleotide, comprising contacting the target polynucleotide with a supramolecular complex as disclosed herein or a metal-ligand complex as disclosed herein under conditions sufficient to inhibit expression of the gene product. In some embodiments, expression of the gene product is inhibited in vivo. In some embodiments, expression of the gene product is inhibited in vitro. In some embodiments, expression of the gene product is inhibited by at least about 5%.

Also provided herein are methods of detecting a target molecule comprising contacting the target molecule with a supramolecular complex as disclosed herein or a metal-ligand complex as disclosed herein, wherein contact between the target molecule and the supramolecular complex or the metal-ligand complex results in a detectable change. In some embodiments, the detecting is in vitro. In some embodiments, the detecting is in vivo.

DETAILED DESCRIPTION

Figure 1:
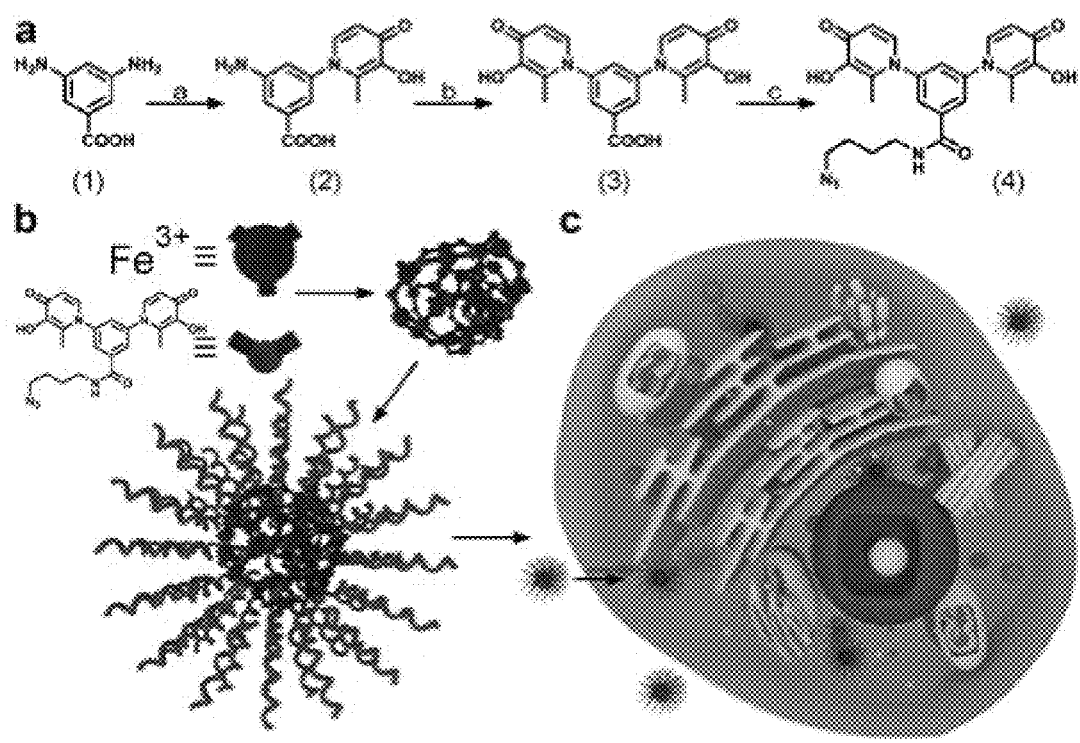
FIG. 1 shows the synthesis and assembly of ICP particles and their cellular uptake. a) Synthetic scheme for bis-3,4-HOPO azide (4). b) Assembly of ICP particles from $Fe(NO_3)_3$ and compound 4, followed by conjugation with DNA via a Cu free 'Click' reaction. c) Scheme depicting the cellular uptake of ICP-DNA conjugates.

Provided herein is a strategy that employs the use of infinite coordination polymer (ICP) nanoparticles made from ferric ions and a rigid ditopic chelating ligand to synthesize novel SNA nanoparticle conjugates.

This disclosure can be used for, e.g., antisense gene regulation, drug delivery, and bio-detection. Several advantages of this disclosure include non-toxic core that disassembles below physiological pH; they are as effective or better than AuNP-SNAs at crossing cell membranes; and the core is assembled from inexpensive building blocks, which make them easy to scale up.

DNA-functionalized infinite coordination polymer (ICP) nanoparticles are disclosed herein as biocompatible gene regulation agents. ICP nanoparticles were synthesized from ferric nitrate and a ditopic 3-hydroxy-4-pyridinone (HOPO) ligand bearing a pendant azide. Addition of Fe(III) to a solution of the ligand produced nanoparticles, which were colloidally unstable in the presence of salts. Conjugation of DNA to the Fe(III)-HOPO ICP particles, via copper-free click chemistry, afforded colloidally stable nucleic acid nanoconstructs. The DNA-ICP particles, when cross-linked through sequence-specific hybridization, exhibit narrow, highly cooperative melting transitions consistent with dense DNA surface loading. The ability of the DNA-ICP particles to enter cells and alter protein expression was also evaluated. Our results indicate these novel particles carry nucleic acids into mammalian cells without the need for transfection agents and are capable of efficient gene knockdown.

Spherical nucleic acids (SNAs) have emerged as an interesting new class of materials that have shown promise in programmable materials synthesis,[1] bio-detection,[2] and intracellular gene regulation. [3] Such structures are often comprised of a nanoparticle core functionalized with a dense layer of oligonucleotides, although hollow, core-free versions have been developed.[4] The earliest example of SNAs involved gold nanoparticles modified with a dense layer of alkylthiol-functionalized DNA,[5] but iron oxide, [6] silver,[7] semiconductor quantum dot,[8] and organic cores have been explored as well.[9] Notably, the chemical and biological properties of SNAs are markedly different from their linear counterparts. SNAs exhibit cooperative binding and sharp thermal denaturation profiles, enter cells without the need for cationic transfection agents, and have the ability to bind to receptors in a polyvalent fashion.[10] Consequently, they are powerful new entities for manipulating cellular processes through gene regulation,[11] drug delivery,[12] and immunomodulatory pathways.[13] The active uptake of SNAs occurs via caveolin-mediated endocytosis, triggered by their binding to class A scavenger receptors (SR-As).[14] Although SNAs made from gold have shown commercial promise as medical diagnostic and research tools and have shown no acute toxicity in vivo,[15] there are concerns about the potential long term toxicity of gold nanoparticles and their metabolic fate.[16] Consequently, new forms of SNAs that have cores made of biocompatible materials are highly sought after. Provided herein is a strategy that employs the use of infinite coordination polymer (ICP) nanoparticles made from ferric ions and a rigid ditopic chelating ligand to synthesize novel SNA nanoparticle conjugates. These DNA-ICPs are designed from chemical building blocks approved by the FDA for other pharmaceutical uses, exhibit cooperative binding, and can readily cross mammalian cell membranes and inhibit protein expression in a targeted fashion.

ICP nanoparticles consist of amorphous networks of organic ligands bridged by metal nodes.[17] They are promising materials for SNA construction as the ligand/metal combination that defines the ICP structure can be rationally designed to optimize the toxicological and pharmacokinetic profiles of the DNA-ICP conjugate. One major limitation of many ICPs designed for medicinal applications is their instability in aqueous buffers. Some researchers have circumvented this limitation by encapsulating the particle core in silica[18] or a shell of lipids.[19] In contrast, provided herein are strategies to design ICP particles that could be synthesized, purified, and stored indefinitely under aqueous conditions and without specialized equipment or reagents. Furthermore, the use of relatively nontoxic metal ions is a crucial requirement for biological applications. These goals were accomplished by synthesizing ICP nanoparticles from strongly chelating 3-hydroxy-4-pyridinone (3,4-HOPO) ligands in combination with $Fe^{III}$, the most abundant transition metal in the body. The coordination chemistry and pharmacology of the 3,4-HOPOs have been systematically investigated,[20] and the 1,2-dimethyl derivative (deferiprone) is FDA-approved for the treatment of iron overload in humans.[21] Furthermore, the Fe(HOPO)$_3$ complex is known to dissociate below physiological pH.[22] This provides a potential release mechanism for delivering DNA into the cytosol following cell entry, a novel property not typically associated with SNAs prepared to date.

It is known that ditopic HOPO and catechol ligands, being isoelectronic, can form insoluble coordination polymers with oxophilic metal cations such as $Fe^{III}$, $Cr^{III}$, $Ga^{III}$ and others, however, such polymers are poorly understood and have not been well-studied in the literature.[23] These ligands have mainly been studied for metal sequestration as opposed to materials synthesis. Therefore, this was an opportunity to construct a novel nanoparticle scaffold for modification with DNA. Specifically, a new ditopic ligand DABA-bis-HP-N$_3$ (4) was prepared, which deliberately employs the inexpensive building blocks maltol and 3,5-diaminobenzoic acid (DABA, 1) (FIG. 1a). Two sequential acid-catalyzed condensations of maltol with DABA (1 to 2; 2 to 3) followed by HATU-mediated amidation of the carboxylic acid afforded the azide-bearing ditopic ligand 4. Importantly, the carboxylic acid in 3 may be amidated with a wide variety of amine building blocks, affording ICP particles with tailorable post-synthetic chemistry dictated by the pendant functional groups.

Figure 2:
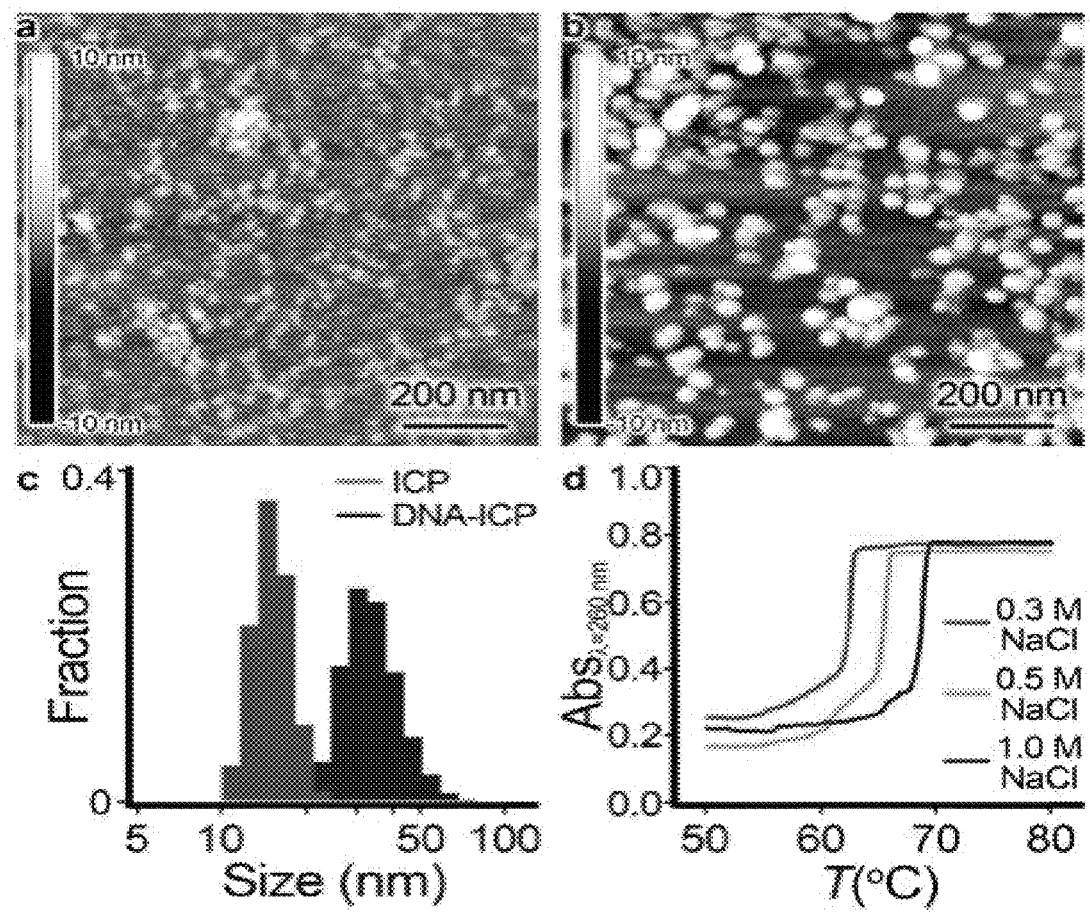
FIG. 2 shows the characterization of DNA-ICP particles. AFM image of (a) Bare ICP particles drop-cast and dried on mica. b) DNA-functionalized ICP particles drop-cast and dried on mica. c) DLS histograms comparing size distributions of bare and DNA-functionalized ICPs. d) Cooperative melting of ICP-DNA aggregates for various salt concentrations.

To synthesize ICP nanoparticles from ligand 4, a dilute NaOH solution of ligand 4 (1.07 mM ligand, 1877 µL) was prepared and injected a solution of ferric nitrate (10.8 mM, 123 µL) into it (FIG. 1b). Particle formation occurs instantaneously and the color of the solution turns from clear to red due to the ligand-metal charge transfer band (LMCT) of the tris-HOPO-$Fe^{III}$ complex (λ.max≈460 nm).[24] The resulting ICP-N$_3$ nanoparticles were colloidally unstable in the presence of low concentrations of salts (NaCl, Tris.HCl), leading to gradual precipitation of a red, insoluble material. The crude ICP-N$_3$ particles were purified by centrifugal filtration (100 kDa molecular weight cut-off) and re-suspended in H$_2$O. The particles are retained on the filter, as they are too large to pass through. Minimal loss of material through the filter indicated a colloidal dispersion of high-molecular weight species was obtained. In deionized H$_2$O, the as-synthesized particles were stable, with a mean hydrodynamic diameter of 10-20 nm, as determined by dynamic light scattering (DLS) (FIG. 2c, left). TEM and AFM imaging revealed aggregates of small nanoparticles, with some degree of fusion occurring upon drying. Furthermore, the composition of the ICP-N$_3$ particles was probed spectroscopically. Aliquots containing a fixed concentration of DABA-bis-HP-N$_3$ ligand in H$_2$O were prepared and treated with increasing amounts of iron ranging from 0 to 1.1 equivalents. The absorbance at 460 nm increased until 0.66 equivalents of $Fe^{III}$ were added, consistent with a metal-ligand stoichiometry of Fe$_2$L$_3$ (see FIG. 5).

For conjugation to bare ICP-N$_3$ particles, all oligonucleotides were made on an automated DNA synthesizer, purified by reverse-phase HPLC, and characterized by MALDI-ToF. Dibenzocyclooctyne (DBCO) phosphoramidites are commercially available and easily incorporated onto the 5' termini of the oligonucleotides. DNA strands modified with a Cyanine 5 (Cy5) dye were used for intracellular imaging studies. DNA strands modified with a 5' alkylthiol were used to construct AuNP-SNAs for comparison with DNA-ICP particles (Table 1).

DBCO-bearing oligonucleotides were conjugated to ICP-N$_3$ particles by simply mixing the two reactants in aqueous NaCl (0.5M) followed by repeated ultrafiltration to remove unreacted DNA. The resulting DNA-ICP particles were suspended in Tris.HCl buffer (100 mM, pH 8.0) and remained colloidally stable indefinitely when stored at 5° C. In contrast, the bare ICP-N$_3$ particles precipitated when stored in a solution of the same ionic strength.

Figure 3:
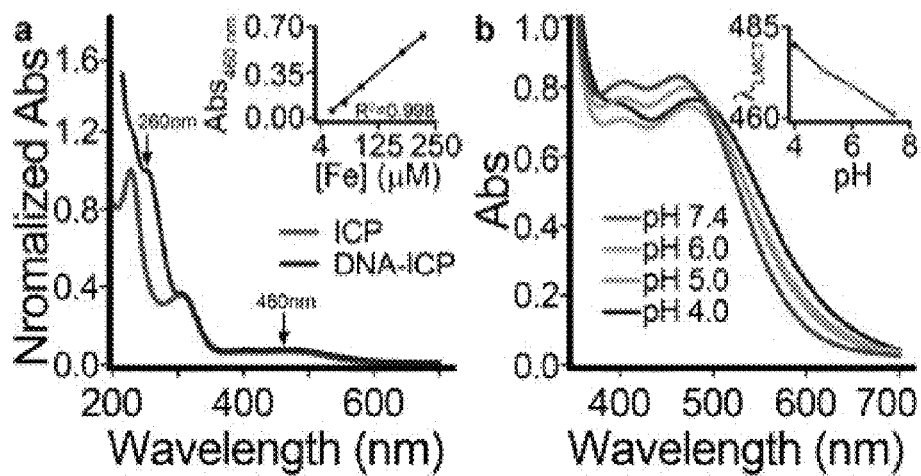
FIG. 3 shows UV-Vis analysis of DNA-ICP particles. a) Comparison of bare ICP particles with DNA-ICP particles showing the change in DNA absorbance at 260 nm. Inset: determination of LMCT extinction coefficient at 460 nm. b) pH dependence of LMCT absorbance. The red-shift of $\lambda_{max}$ with decreasing pH is indicative of complex dissociation (see inset).

In addition to exhibiting colloidal stability, the DNA-ICP nanoparticles also were found to differ in size, surface charge, and morphology as compared to the bare ICP-N$_3$ particles. DLS and zeta potential measurements showed a consistent increase in hydrodynamic diameter (FIG. 2c, right) and surface charge, respectively. In addition, UV-Vis spectroscopy could be used to calculate the relative contribution of DNA to the absorbance at 260 nm, and hence the DNA concentration could be determined. Inductively-coupled plasma mass spectrometry (ICP-MS) was also used to calculate directly the extinction coefficient $\epsilon 460$ of the ICP particles (FIG. 3a). Additionally, particles were imaged by AFM after conjugation with DNA to visualize changes in size and morphology (FIG. 2a,b). Lastly, incubation of DNA-ICP particles in aqueous buffers ranging from physiological pH (7.4) to low lysosomal pH (4.0) showed a clear red-shift in the LMCT $\lambda_{maxi}$, indicating partial dissociation of the tris-coordinated $Fe^{III}$ nodes comprising the particle (FIG. 3b).

In order to probe the surface density of oligonucleotides on the DNA-ICP particles, thermal denaturation experiments were carried out wherein ICPs with complementary sequences (A-ICP and B-ICP) were mixed, allowed to hybridize, and then heated above the melting transition of the duplex. The free double-stranded DNA duplex possesses a 17 base-pair overlap with $T_m$=54.0° C. in 0.3M NaCl. In contrast, the same complementary strands form duplexes with a $T_m$=66.9° C. when conjugated to ICP-N3 particles, an increase of nearly 13° C. In addition, the melting transition of the DNA-ICP particle aggregates is extremely narrow, a hallmark signature of cooperativity; the full width at half-maximum (FWHM) of the melting curve is typically <2° C., compared to 10-20° C. for free double-stranded DNA. A-ICP and B-ICP particles were melted at salt concentrations ranging from 0.1M to 1M NaCl, showing an increase in $T_m$ with increasing ionic strength. (FIG. 2d). As a control experiment, A-ICP particles alone exhibited no aggregation or melting under the experimental conditions, nor did A-ICP particles mixed with non-complementary particles (NonTarget-ICP).

The interaction of DNA-ICP particles with conventional AuNP-SNAs was also studied, to determine if the DNA-ICP particles possess DNA recognition and binding properties similar to their gold counterparts. Gold nanoparticles (15 nm, Ted Pella) were functionalized with alkylthiol modified oligonucleotides A-SH and purified according to established protocols to afford A-AuNP particles.[25] When A-AuNP and B-ICP particles were mixed in a 1:1 ratio, aggregation was observed with a concomitant broadening and red-shift of the AuNP plasmon resonance at $\lambda_{max} \approx 520$ nm. Thermal denaturation curves were collected at salt concentrations ranging from 0.3 to 0.7M NaCl. As a control, non-complementary mismatched particles A-AuNP and A-ICP were also mixed and, as anticipated, did not exhibit aggregation or melting behavior (see FIG. 6). Overall, the thermal denaturation studies qualitatively suggest high DNA surface loading on the ICP-$N_3$ particles. Previous studies showed that sharp thermal denaturation curves (FWHM<2° C.) only arise when oligonucleotide loading approaches or exceeds approximately 50 strands on a 10 nm particle core.[6a]

TABLE 1

Oligonucleotide Sequences

| Oligo Name | Sequence | SEQ ID NO: |
|---|---|---|
| A-DBCO | 5'-DBCO-TEG-$A_4$-AATCCTTATCAATAT TT-3' | 1 |
| B-DBCO | 5'-DBCO-TEG-$A_4$-AAATATTGATAAGGA TT-3' | 2 |
| A-SH | 5'-HS-$(CH_2)_6$-$A_4$-AATCCTTATCAATAT TT-3' | 3 |
| Her2-DBCO | 5'-DBCO-CTCCATGGTGCTCAC-3' | 4 |
| NonTarget-DBCO | 5'-DBCO-CTCCTTCACCTTCGCGCAGC-3' | 5 |
| Cy5-DBCO | 5'-DBCO-TEG-CCTCCTCCT-Cy5-CCTC CTCCT-3' | 6 |
| Cy5-SH | 5'-HS-$(CH_2)_6$-CCTCCTCCT-Cy5-CCTC CTCCT-3' | 7 |

Due to the high apparent oligonucleotide density on the DNA-ICP surface, it was hypothesized that they would function as efficient gene delivery agents, much like their gold predecessors.[3] To test this assumption, ICP-$N_3$ particles were functionalized with the poly(CCT) oligonucleotide Cy5-DBCO bearing an internal fluorophore-label to afford Cy5-ICP particles. Likewise, gold nanoparticles (15 nm) were functionalized with the analogous Cy5-SH oligonucleotide to afford Cy5-AuNP particles having a loading of approximately 113 strands per AuNP, as determined by fluorescence measurements.

Figure 4:
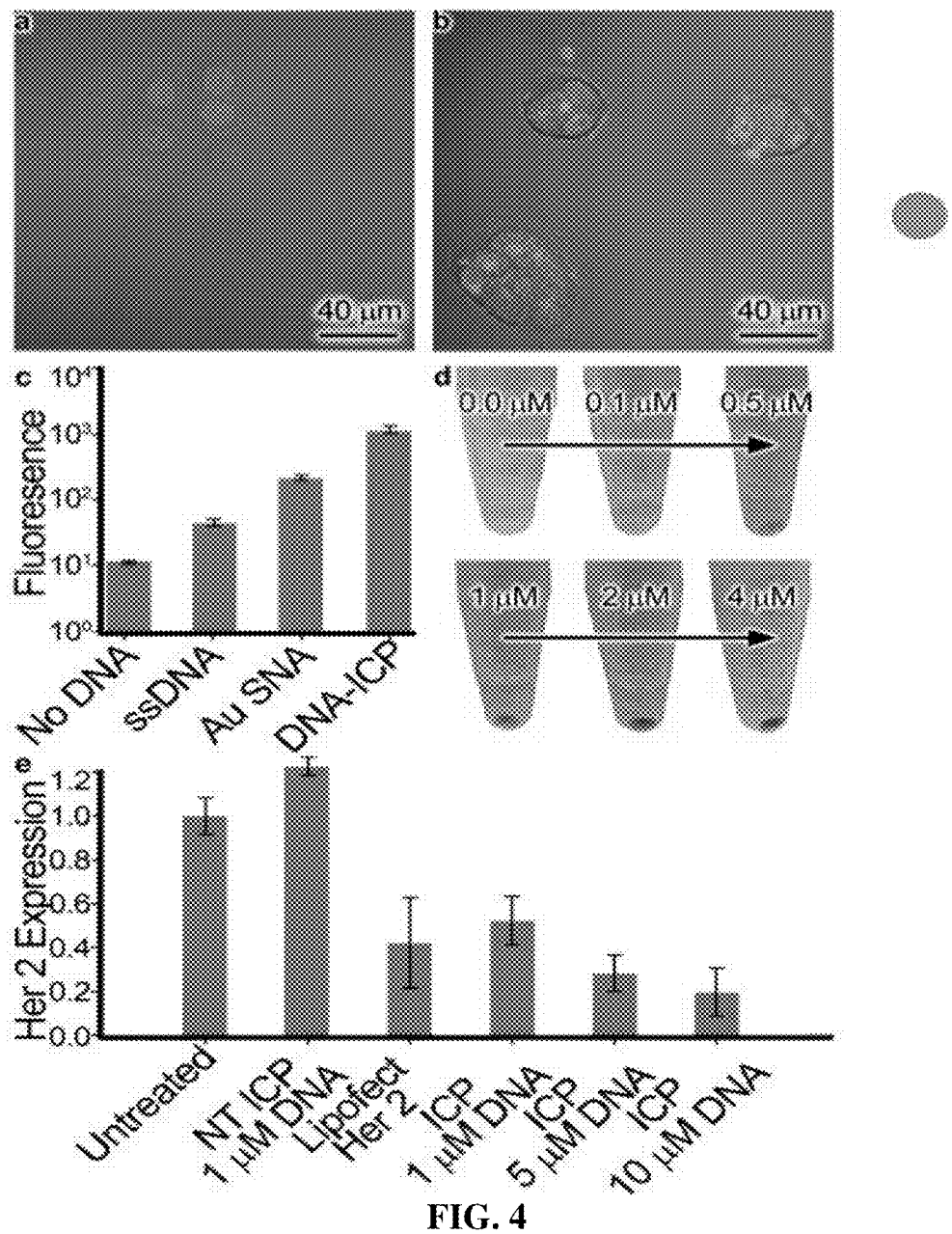
FIG. 4 shows cellular uptake and gene knockdown. Confocal microscopy image of C166 cells treated with (a) Cy5-ssDNA and (b) DNA-ICP particles (100 nM DNA in each case). Hoechst stain denotes the nucleus in blue while the Cy5 dye attached to the DNA is in red. c) Fluorescence intensity of Cy5 dye quantified by flow cytometry. d) Naked-eye visualization of DNA-ICPs taken up in pelleted MCF-7 breast cancer cells e) Expression of HER2 protein in SKOV-3 cells treated with non-targeting DNA-ICPs, HER2 targeting ssDNA+Lipofectamine, and HER2 targeting DNA-ICPS.

Uptake was examined in HeLa cervical cancer cells by confocal microscopy (FIG. 3a,b) and flow cytometry (FIG. 4c). The DNA-ICP particles were found to cross cell membranes more efficiently than the free DNA strands, and exhibited comparable uptake to AuNP-SNA nanoparticles [26] bearing the same sequence. These results suggest that DNA-ICP nanoparticles have the potential to transport large amounts of DNA, in particle-bound or free form, to the cytosol. Furthermore, a dose-dependent increase in iron concentration was found after incubation of DNA-ICPs in MCF-7 breast cancer cells for 24 hours. The color of the iron complex could be seen by the naked eye in pelleted cells treated with DNA-ICPs (FIG. 4d). Additional confocal microscopy experiments with C166 mouse endothelial cells confirmed that DNA-ICPs readily enter numerous cell lines without the need for transfection agents.

Having demonstrated the ability of DNA-ICP conjugates to enter cells in a manner analogous to AuNP-SNAs, their ability to alter protein expression by targeting a known cancer-related mRNA transcript was investigated. As a proof-of-concept, SKOV-3 ovarian cancer cells were chosen as they over-express human epithelial growth factor receptor 2 (HER2), which is involved in signal transduction pathways leading to malignant cell growth and differentiation. [27] A series of gene knockdown experiments was performed utilizing anti-HER2 DNA-ICPS. SKOV-3 cells were incubated with different concentrations of antisense DNA-ICPS (HER2-ICP) or non-targeting DNA-ICPS (NonTarget-ICP), with free anti-HER2 DNA complexed with Lipofectamine® (Life Technologies) as a positive control. After 3 days, cells were harvested and HER2 expression was determined by Western blot analysis (FIG. 4e). These results indicate that the anti-HER2 DNA-ICPs reduce HER2 expression by 55-81% depending on the DNA concentration (1-10 μM). This is comparable to results achieved with commercial transfection agents, and furthermore no change in HER2 expression was observed with non-targeting DNA-ICPs. Lastly, no toxic effects or cell death resulted from treatment with DNA-ICPS, as predicted by MTT assays.

In conclusion, provided herein is a facile method to synthesize biocompatible, DNA-decorated infinite coordination polymer nanoparticles that are capable of cell entry and gene regulation without transfection agents. Iron(III)-based ICP nanoparticles, synthesized in water, can be conjugated directly to oligonucleotides and carry them across cell membranes. Furthermore, the core is comprised of benign building blocks that are not expected to pose significant health hazards. This work represents a major step towards the construction of clinically viable gene regulation constructs for in vivo applications in the treatment of cancer and other genetic diseases.

Metal-Ligand Complexes

In various aspects, the present disclosure provides a metal-ligand complex of Fe(III) and a compound of structure

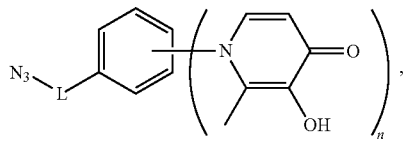

with substituents as disclosed herein. In some cases, the metal-ligand complex is an infinite coordination polymer of general formula $Fe_2(Compound)_3$. In various cases, the metal-ligand complex can further comprise a polynucleotide attached via a surface azide from one Compound, to form a structure with the azide of the surface Compound of

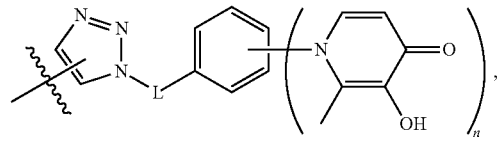

wherein L is $C_{1-20}$alkylene or —C(O)NH—$C_{1-20}$alkylene; and n is 1 or 2. The polynucleotide can comprise an alkyne (e.g., a DBCO) at a terminus of the polynucleotide for attachment to the azide of the surface Compound.

Polynucleotides containing moieties as disclosed herein at a terminus can be obtained by attaching the moiety to polynucleotides modified to have reactive functional groups. For example, an aminoalkyl-modified polynucleotide can be attached to a ligand or ligand precursor having a carboxylic acid group or an activated carboxylic acid group. Suitable reagents for activating carboxylic acid groups include, but are not limited to, carbodiimides (e.g., dicyclohexylcarbodiimide, diisopropylcarbodiimide, 1-ethyl-3-[3-dimethylaminopropyl]carbodiimide, phenyl ethyl carbodiimide, phenyl isopropyl carbodiimide), benzotriazoles (e.g., 1-hydroxy-1H-benzotriazole, 1-hydroxy-7-azabenzotriazole, O-(7-azabenzotriazol-1-yl)-1,1,3,3-tetra-methyluronium hexafluorophosphate, O-(benzotriazol-1-yl)-1,1,3,3-tetramethyluronium hexafluorophosphate), and mixtures thereof.

In some cases, the polynucleotide is modified at a terminus with a DBCO-type moiety for reaction with the azide of the HOPO-ligand:

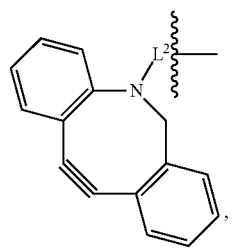

where L is a linker to a terminus of the polynucleotide. $L^2$ can be $C_{1-10}$ alkylene, —C(O)—$C_{1-10}$ alkylene-Y—, and —C(O)—$C_{1-10}$ alkylene-Y—$C_{1-10}$ alkylene-(OCH$_2$CH$_2$)$_m$—Y—; wherein each Y is independently selected from the group consisting of a bond, C(O), O, NH, C(O)NH, and NHC(O); and m is 0, 1, 2, 3, 4, or 5. For example, the DBCO functional group can be attached via a linker having a structure of

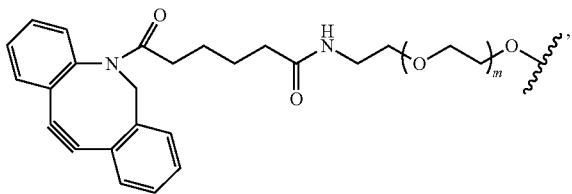

where the terminal "O" is from a terminal nucleotide on the polynucleotide.

The metal-ligand complex typically is prepared by combining a solution of a azide Compound as described herein with a solution of $Fe^{3+}$ in a suitable solvent. Generally, the molar ratio of $Fe^{3+}$ to Compound when combined in the solvent is at least 1:10, for example, at least 1:5, at least 1:3, at least 1:2, at least 1:1.5, at least 1:1, at least 1:0.75, at least 1:0.5, at least 1:0.25, and/or at least 1:0.1. Suitable solvents include, but are not limited to, water and aqueous buffer solutions such as phosphate buffered saline. Generally, the pH of the solvent is about 6 to about 11, for example, about 7 to about 10, about 7 to about 9, and/or about 7 to about 8. Then the polynucleotide with an alkyne moiety at one terminus is reacted with the metal-ligand complex to attach to via a surface azide.

In various aspects, the present disclosure provides a supramolecular complex comprising a first metal-ligand complex as described herein and a second metal-ligand complex as described herein, wherein the polynucleotide of the first metal-ligand complex and polynucleotide of the second metal-ligand complex are sufficiently complementary to hybridize under appropriate conditions. In various embodiments, the supramolecular complex comprises the first polynucleotide hybridized with the second polynucleotide. In some embodiments, the melting temperature ($T_m$) of the hybridized first and second polynucleotides within the supermolecular complex is at least about 30° C., at least about 35° C., at least about 40° C., at least about 45° C., at least about 50° C., at least about 55° C., at least about 60° C., at least about 65° C., at least about 70° C., at least about 75° C., at least about 80° C., at least about 85° C., at least about 90° C., at least about 95° C., and/or at least about 100° C. The supramolecular complexes typically are present as nanoparticles having an average particle diameter of about 1 nm to about 1000 nm, for example, about 2 nm to about 900 nm, about 3 nm to about 800 nm, about 4 nm to about 700 nm, about 5 nm to about 600 nm, about 5 nm to about 500 nm, about 5 nm to about 400 nm, about 5 nm to about 300 nm, about 5 nm to about 200 nm, about 10 nm to about 200 nm, about 10 nm to about 100 nm, about 10 nm to about 90 nm, about 10 nm to about 80 nm, about 10 nm to about 70 nm, about 10 nm to about 60 nm, about 10 nm to about 50 nm, about 20 nm to about 40 nm, and/or about 30 nm.

Supramolecular complexes typically are prepared by combining a solution of a first polynucleotide-metal-ligand complex with a solution of a second polynucleotide-metal-ligand complex in a suitable solvent to form the supermolecular complex via hybridization of the first polynucleotide and the second polynucleotide due to their sufficient complementarity. The solutions can further include sodium chloride.

In various aspects, the present disclosure provides a method of inhibiting expression of a gene product encoded by a target polynucleotide comprising contacting the target polynucleotide with a supramolecular complex or metal-ligand complex as described herein under conditions sufficient to inhibit expression of the gene product. In some embodiments, expression of the gene product is inhibited in vivo. In some embodiments, expression of the gene product is inhibited in vitro. In various embodiments, expression of the gene product is inhibited by at least about 5% relative to expression of the gene product in the absence of contacting the target polynucleotide with the supramolecular complex or metal-ligand complex, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, and/or at least about 95%. In various aspects, the present disclosure also provides a method of detecting a target molecule comprising contacting the target molecule with a supramolecular complex or metal-ligand complex as described herein, wherein contact between the target molecule and the supramolecular complex or metal-ligand complex results in a detectable change. In some embodiments, the detecting is in vitro. In some embodiments, the detecting is in vivo.

Polynucleotides

Polynucleotides contemplated by the present disclosure include DNA, RNA, modified forms and combinations thereof as defined herein. Accordingly, in some aspects, the metal-ligand complex, supramolecular complex, or nanoparticle comprises DNA. In some embodiments, the DNA is double stranded, and in further embodiments the DNA is single stranded. In further aspects, the metal-ligand complex, supramolecular complex, or nanoparticle comprises RNA, and in still further aspects the metal-ligand complex, supramolecular complex, or nanoparticle comprises double stranded RNA, and in a specific embodiment, the double stranded RNA agent is a small interfering RNA (siRNA). The term "RNA" includes duplexes of two separate strands, as well as single stranded structures. Single stranded RNA also includes RNA with secondary structure. In one aspect, RNA having a hairpin loop in contemplated.

In some aspects, the polynucleotide is comprised of a sequence that is sufficiently complementary to a target sequence of a polynucleotide such that hybridization of the polynucleotide that is part of the metal-ligand complex, supramolecular complex, or nanoparticle and the target polynucleotide takes place. The polynucleotide in various aspects is single stranded or double stranded, as long as the double stranded molecule also includes a single strand sequence that hybridizes to a single strand sequence of the target polynucleotide. In some aspects, hybridization of the polynucleotide that is part of the metal-ligand complex, supramolecular complex, or nanoparticle can form a triplex structure with a double-stranded target polynucleotide. In another aspect, a triplex structure can be formed by hybridization of a double-stranded polynucleotide that is part of a metal-ligand complex, supramolecular complex, or nanoparticle to a single-stranded target polynucleotide. Further description of triplex polynucleotide complexes is found in PCT/US2006/40124, which is incorporated herein by reference in its entirety.

A "polynucleotide" is understood in the art to comprise individually polymerized nucleotide subunits. The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases adenine (A), guanine (G), cytosine (C), thymine (T) and uracil (U). Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-triazolopyridine, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleotides include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5, 4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example, 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No.

7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

The metal-ligand complexes and supramolecular complexes generally comprise a polynucleotide from about 5 nucleotides to about 500 nucleotides in length, or 5 to about 100 nucleotides. More specifically, metal-ligand complexes and supramolecular complexes comprise polynucleotides that are about 5 to about 90 nucleotides in length, about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated.

Polynucleotides, as defined herein, also includes aptamers. The production and use of aptamers is known to those of ordinary skill in the art. In general, aptamers are nucleic acid or peptide binding species capable of tightly binding to and discreetly distinguishing target ligands (Yan et al., RNA Biol. 6(3) 316-320 (2009), incorporated by reference herein in its entirety). Aptamers, in some embodiments, may be obtained by a technique called the systematic evolution of ligands by exponential enrichment (SELEX) process (Tuerk et al., Science 249:505-10 (1990), U.S. Pat. No. 5,270,163, and U.S. Pat. No. 5,637,459, each of which is incorporated herein by reference in their entirety). General discussions of nucleic acid aptamers are found in, for example and without limitation, Nucleic Acid and Peptide Aptamers: Methods and Protocols (Edited by Mayer, Humana Press, 2009) and Crawford et al., Briefings in Functional Genomics and Proteomics 2(1): 72-79 (2003). Additional discussion of aptamers, including but not limited to selection of RNA aptamers, selection of DNA aptamers, selection of aptamers capable of covalently linking to a target protein, use of modified aptamer libraries, and the use of aptamers as a diagnostic agent and a therapeutic agent is provided in Kopylov et al., Molecular Biology 34(6): 940-954 (2000) translated from Molekulyarnaya Biologiya, Vol. 34, No. 6, 2000, pp. 1097-1113, which is incorporated herein by reference in its entirety. In various aspects, an aptamer is between 10-100 nucleotides in length.

In various aspects, the methods include use of a polynucleotide which is 100% complementary to the target polynucleotide, i.e., a perfect match, while in other aspects, the polynucleotide is at least (meaning greater than or equal to) about 95% complementary to the target polynucleotide over the length of the polynucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the target polynucleotide over the length of the polynucleotide to the extent that the polynucleotide is able to achieve the desired of inhibition of a target gene product. It will be understood by those of skill in the art that the degree of hybridization is less significant than a resulting detection of the target polynucleotide, or a degree of inhibition of gene product expression.

Polynucleotide Density

Metal-ligand complexes and supramolecular complexes as provided herein have a density of the polynucleotide on the surface of the complex. In some aspects, the resistance of the polynucleotide to degradation and/or the uptake of nanoparticles by a cell is influenced by the density of polynucleotides associated with the complex. As described in PCT/US2008/65366, incorporated herein by reference in its entirety, a higher density of polynucleotides on the surface of a polynucleotide functionalized complex is associated with an increased uptake of complex by a cell.

A surface density adequate to make the complex stable and the conditions necessary to obtain it for a desired combination of complexes and polynucleotides can be determined empirically. Broadly, the smaller the polynucleotide that is used, the higher the surface density of that polynucleotide can be. Generally, a surface density of at least 1 pmol/cm$^2$ will be adequate to provide stable complex. In some aspects, the surface density is at least 10 pmol/cm$^2$. Methods are also provided wherein the polynucleotide is present in a nanoparticle at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^{2t}$ at least 8 pmol/cm$^2$, at least 9 pmol/cm$^2$, at least 10 pmol/cm$^2$, at least about 15 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^{2t}$ at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^{2t}$ at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more.

It is contemplated that the density of polynucleotides in a complex modulates specific biomolecule and/or non-biomolecule interactions with the polynucleotide on the surface and/or with the complex itself. Under various conditions, some polypeptides may be prohibited from interacting with polynucleotides that are part of a complex based on steric hindrance caused by the density of polynucleotides. In aspects where interaction of polynucleotides with a biomolecule and/or non-biomolecule that are otherwise precluded by steric hindrance is desirable, the density of polynucleotides in the complex is decreased to allow the biomolecule and/or non-biomolecule to interact with the polynucleotide.

It is also contemplated that polynucleotide surface density modulates the stability of the polynucleotide associated with the complex. Thus, in one embodiment, a complex comprising a polynucleotide is provided wherein the polynucleotide has a half-life that is at least substantially the same as the half-life of an identical polynucleotide that is not part of a complex. In other embodiments, the polynucleotide associated with the complex has a half-life that is about 5% greater to about 1,000,000-fold greater or more than the half-life of an identical polynucleotide that is not part of a complex.

Methods of Detecting a Target Polynucleotide

The disclosure provides methods of detecting a target molecule comprising contacting the target molecule with a complex as described herein. The contacting results, in various aspects, in regulation of gene expression as provided by the disclosure. In another aspect, the contacting results in a detectable change, wherein the detectable change indicates the detection of the target molecule. Detection of the detectable label is performed by any of the methods described herein, and the detectable label can be on a molecule that is part of a metal-ligand complex or supramolecular complex or can be on the target molecule.

Methods of Inhibiting Gene Expression

Additional methods provided by the disclosure include methods of inhibiting expression of a gene product expressed from a target polynucleotide comprising contacting the target polynucleotide with a complex as described herein, wherein the contacting is sufficient to inhibit expression of the gene product. Inhibition of the gene product results from the hybridization of a target polynucleotide with a complex of the disclosure.

It is understood in the art that the sequence of a polynucleotide that is part of a metal-ligand complex or supramolecular complex need not be 100% complementary to that of its target polynucleotide in order to specifically hybridize to the target polynucleotide. Moreover, a polynucleotide that is part of a metal-ligand complex or supramolecular complex may hybridize to a target polynucleotide over one or more segments such that intervening or adjacent segments are not involved in the hybridization event (for example and without limitation, a loop structure or hairpin structure). The percent complementarity is determined over the length of the polynucleotide that is part of the metal-ligand complex or supramolecular complex. For example, given a metal-ligand complex or supramolecular complex comprising a polynucleotide in which 18 of 20 nucleotides of the polynucleotide are complementary to a 20 nucleotide region in a target polynucleotide of 100 nucleotides total length, the polynucleotide that is part of the metal-ligand complex or supramolecular complex would be 90 percent complementary. In this example, the remaining noncomplementary nucleotides may be clustered or interspersed with complementary nucleotides and need not be contiguous to each other or to complementary nucleotides. Percent complementarity of a polynucleotide that is part of a metal-ligand complex or supramolecular complex with a region of a target polynucleotide can be determined routinely using BLAST programs (basic local alignment search tools) and Power-BLAST programs known in the art (Altschul et al., J. Mol. Biol., 1990, 215, 403-410; Zhang and Madden, Genome Res., 1997, 7, 649-656).

Methods for inhibiting gene product expression include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of a metal-ligand complex or supramolecular complex comprising a polynucleotide. In other words, methods provided embrace those which result in essentially any degree of inhibition of expression of a target gene product.

The degree of inhibition is determined in vivo from a body fluid sample or from a biopsy sample or by imaging techniques well known in the art. Alternatively, the degree of inhibition is determined in vitro in a cell culture assay, generally as a predictable measure of a degree of inhibition that can be expected in vivo resulting from use of a composition as described herein. It is contemplated by the disclosure that the inhibition of a target polynucleotide is used to assess the effects of the inhibition on a given cell. By way of non-limiting examples, one can study the effect of the inhibition of a gene product wherein the gene product is part of a signal transduction pathway. Alternatively, one can study the inhibition of a gene product wherein the gene product is hypothesized to be involved in an apoptotic pathway.

It will be understood that any of the methods described herein can be used in combination to achieve a desired result. For example and without limitation, methods described herein can be combined to allow one to both detect a target polynucleotide as well as regulate its expression. In some embodiments, this combination can be used to quantitate the inhibition of target polynucleotide expression over time either in vitro or in vivo. The quantitation over time is achieved, in one aspect, by removing cells from a culture at specified time points and assessing the relative level of expression of a target polynucleotide at each time point. A decrease in the amount of target polynucleotide as assessed, in one aspect, through visualization of a detectable label, over time indicates the rate of inhibition of the target polynucleotide.

Thus, determining the effectiveness of a given polynucleotide to hybridize to and inhibit the expression of a target polynucleotide, as well as determining the effect of inhibition of a given polynucleotide on a cell, are aspects that are contemplated.

EXAMPLES

General Materials and Methods: 3,5-Diaminobenzoic acid was purchased from TCI America (Portland, Oreg.). 4-Azido-butan-1-amine was purchased from Synthonix, Inc. (Wake Forest, N.C.). All reagents for oligonucleotide synthesis were purchased from Glen Research (Sterling, Va.) and used according to manufacturer instructions. Buffer solutions were purchased from Invitrogen (Carlsbad, Calif.). Deuterated solvents were purchased from Cambridge Isotope Laboratories Inc. (Andover, Mass.). Gold nanoparticles were purchased from Ted Pella (Redding, Calif.). Amicon® Ultra centrifugal filter units were purchased from EMD Millipore (Billerica, Mass.). All other reagents were purchased from Sigma-Aldrich (St. Louis, Mo.) and used without further purification. $^1$H NMR spectra were recorded on a Bruker Avance 400 MHz NMR spectrometer. $^1$H NMR spectra were referenced internally to residual proton signals in the deuterated solvents. $^{13}$C NMR spectra for compounds 3 and 4 were collected on an Agilent DD2 500 MHz NMR spectrometer operating at an internal temperature of 100° C. Electrospray ionization (ESI) mass spectra were recorded on an Agilent 6120 LC-TOF instrument in positive ionization mode. UV-Vis spectra and thermal denaturation curves were collected on an Agilent Cary 5000 UV-Vis spectrometer in quartz cuvettes having a path length of 1 cm. Matrix-assisted laser desorption/ionization time-of-flight (MALDI-ToF) data was collected on a Bruker AutoFlex III MALDI-ToF mass spectrometer employing 2,5-dihydroxyacetophenone (DHAP) as the matrix material. FTIR spectra were collected on a Perkin-Elmer Spectrum 100 FTIR spectrometer. AFM images were collected on a Bruker Dimension Icon atomic force microscope in non-contact mode equipped with a POINTPROBE-PLUS® Silicon-SPM-Sensor. TEM images were collected on a Hitachi H8100 transmission electron microscope operating at an accelerating voltage of 200 kV. TEM and EDX data were collected on a Hitachi HD2300 STEM equipped with two Thermo Scientific X-ray EDX detectors. Dynamic light scattering (DLS) and zeta potential measurements were collected on a Zetasizer Nano ZS (Malvern Instruments Ltd). ICP-MS data were collected on a Thermo X-series II ICP-MS. Elemental analysis was conducted off-site by Intertek Pharmaceutical Services (Whitehouse, N.J.).

mmol), and 30 mL of acidic 2-ethoxyethanol (49:1 ethoxyethanol/12M HCl). The reaction vessel was fitted with a water-cooled condenser and the mixture heated to reflux for 64 h. The resulting suspension was vacuum-filtered while hot and the solids washed with water (50 mL), followed by acetone (50 mL), to afford the crude product as a fine brown solid. The bis product was selectively isolated by precipitation from boiling pyridine (100 mL), filtration, and further precipitation from hot dimethylformamide (100 mL) and drying in vacuo to afford 0.98 g of (3) (2.66 mmol, 12%) as a grey powder sparingly soluble in methanol, soluble in hot DMSO and DMF. $^1$H NMR (400 MHz, DMSO-d6) δ 8.03 (d, J=2.0 Hz, 2H), 8.00 (t, J=2.0 Hz, 1H), 7.64 (d, J=7.4 Hz, 2H), 6.22 (d, J=7.4 Hz, 2H), 2.02 (s, 6H). $^{13}$C NMR (126 MHz, DMSO-d6) δ 170.43, 165.59, 145.52, 142.92, 138.79, 138.26, 134.82, 130.74, 130.47, 128.55, 111.45, 111.28, 13.79, 13.60. HRMS-ESI (m/z): [M+H]$^+$ calculated for C19H17N2O6 369.1081. found 369.1084.

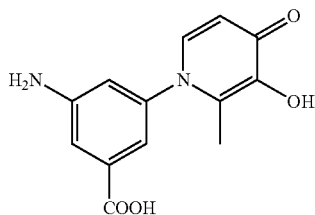 [SMILES: Cc1c(O)c(=O)ccn1-c1cc(N)cc(C(=O)O)c1]

Diaminobenzoic Acid Mono-Hydroxypyridinone (2)

To a 100 mL round-bottomed flask with a magnetic stirrer was added 3,5-diaminobenzoic acid (5.00 g, 32.86 mmol), maltol (8.70 g, 69.00 mmol) and 30 mL of acidic n-propanol (49:1 propanol/12M HCl). The reaction vessel was fitted with a water-cooled condenser and the mixture heated to reflux for 16 h. The resulting suspension was vacuum-filtered while hot and the solids washed with acetone (200 mL) to yield 4.84 g of (2) as a tan powder (18.60 mmol, 57%). Propanol may be substituted with 5:1 EtOH/H$_2$O affording similar yields. $^1$H NMR (400 MHz, DMSO-d6) δ 7.52 (d, J=7.4 Hz, 1H), 7.28-7.26 (m, 1H), 6.92 (t, J=1.7 Hz, 1H), 6.67 (t, J=2.1 Hz, 1H), 6.16 (d, J=7.3 Hz, 1H), 5.77 (s, 2H), 1.96 (s, 3H). $^{13}$C NMR (101 MHz, DMSO-d6) δ 169.96, 167.24, 150.62, 145.45, 142.79, 138.07, 133.21, 129.02, 115.64, 115.35, 114.34, 111.30, 13.61. HRMS-ESI (m/z): [M+H]$^+$ calculated for C13H13N2O4 261.0870. found 261.0875.

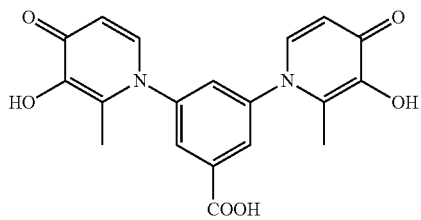 [SMILES: Cc1c(O)c(=O)ccn1-c1cc(C(=O)O)cc(-n2ccc(=O)c(O)c2C)c1]

Diaminobenzoic Acid Bis-Hydroxypyridinone (3)

To a 100 mL round-bottomed flask with a magnetic stirrer was added (2) (5.90 g, 22.67 mmol), maltol (3.57 g, 28.34

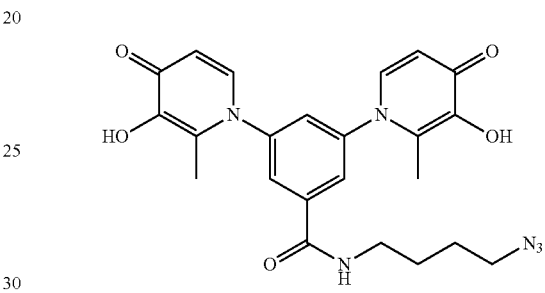

Diaminobenzoic Acid Bis-HP Azide (4)

To a 50 mL round-bottomed flask with a magnetic stirrer was added (3) (0.400 g, 1.09 mmol) fully dissolved in anhydrous DMSO (30 mL). HATU (0.414 g, 1.09 mmol) and diisopropylethylamine (0.48 mL, 2.73 mmol) were subsequently added and the reaction vessel was capped with a rubber septum. After 5 minutes, 4-azidobutan-1-amine (0.187 g, 1.64 mmol) was injected via syringe and the mixture allowed to stir for 4 h under N$_2$. The organic phase was diluted with 1 volume of water and allowed to stand for 1 h. The resulting grey precipitate was collected by vacuum filtration and washed extensively with water (150 mL), followed by acetonitrile (100 mL), and allowed to dry on the filter. The obtained azide monomer (4) was used without further purification. (0.283 g, 0.61 mmol, 56%). $^1$H NMR (400 MHz, DMSO-d6) δ 8.72 (t, J=5.7 Hz, 1H), 8.00 (d, J=2.0 Hz, 2H), 7.91 (t, J=1.9 Hz, 1H), 7.63 (d, J=7.3 Hz, 2H), 6.23 (d, J=7.4 Hz, 2H), 3.41-3.19 (m, 4H), 2.03 (s, 6H), 1.60-1.53 (m, 4H). $^{13}$C NMR (126 MHz, DMSO-d6) δ 170.41, 164.21, 145.55, 142.74, 138.81, 138.27, 137.87, 128.68, 128.54, 126.92, 126.78, 111.39, 111.23, 51.14, 39.56, 26.72, 26.37, 13.81, 13.62. HRMS-ESI (m/z): [M+H]$^+$ calculated for C23H25N6O5 465.1881. found 465.1881. FTIR (KBr): v$_{max}$, 2093 cm$^{-1}$ (N=N=N stretch).

Synthesis of DABA-Bis-HP-N3 ICP Particles (ICP-N3 NPs)

In a typical experiment, an aqueous stock solution of DABA-bis-HP-N3 was prepared consisting of 2.28 mM ligand and 24.5 mM NaOH. The ligand is freely soluble in water as its disodium salt. A stock solution of Fe(NO$_3$)$_3$·9H$_2$O was prepared consisting of 10.80 mM Fe$^{3+}$ and 4 mM HCl (as stabilizer). To a glass vial was added 877 μL ligand stock solution, followed by 1 mL Milli-Q H$_2$O, followed by 123 μL Fe(III) stock and the resulting orange-red mixture (2 mL) shaken for 10 minutes. The as-synthesized particles have a mean diameter ranging from 10-20 nm (DLS). Particles were purified by filtration through an Amicon Ultra 15 mL centrifugal filter with a nominal molecular weight cutoff (MWCO) of 100 kDa, washing with 3×3 mL portions of Milli-Q H2O, spinning at 5000 rcf for 10 minutes each. The particles were resuspended in 2 mL of H2O to give an approximate azide concentration of 1 mM. The particle solution was lyophilized and the resulting dark red powder characterized by FTIR (KBr), showing the characteristic azide stretch at 2093 cm$^{-1}$ is retained after the nanoparticle synthesis.

Figure 5:
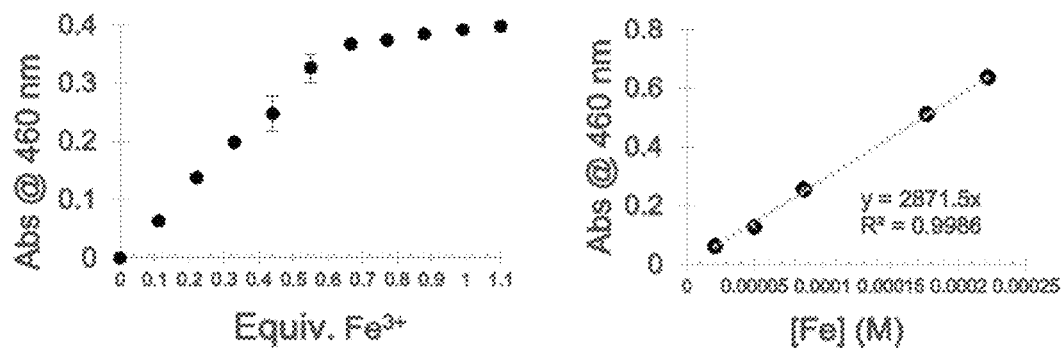
FIG. 5 shows left: titration of ligand 4 with iron(III); and right: determination of $\epsilon_{460}$ of ICP-N3 particles.

Characterization of ICP-N3 Nanoparticles: To determine the stoichiometry of metal-ligand binding, we conducted a titration wherein samples each containing a fixed concentration of 200 uM DABA-bis-11P-N3 (4) in 1 mL H$_2$O were prepared with increasing amounts of Fe(NO$_3$)$_3$.9H$_2$O ranging from 0 to 220 μM. The absorbance at 460 nm was measured for each sample. The LMCT band at 460 nm is characteristic of the tris-HOPO-Fe$^{3+}$ coordination complex. The equivalence point was reached at 133 μM (0.66 equiv.), consistent with Fe$_2$L$_3$ stoichiometry (FIG. 5). Further increase in absorbance is due to the presence of uncoordinated iron precursor salt. Additionally, we conducted elemental analysis on a lyophilized sample of the particles to assess their composition. Calc'd for C69H66Fe2N18O15: C, 55.28%, H, 4.44%, N, 16.82%. Found C, 49.10%, H, 4.18%; N, 14.18%. The lower observed organic content may be explained by the porous nature of the ICP particles and their ability to entrap polar solvent molecules, e.g. H$_2$O. Lastly, we studied the bare ICPs by energy dispersive X-ray spectroscopy (Hitachi H2300-A STEM).

ICP-MS and UV-Vis were used in tandem to determine the extinction coefficient ($\epsilon_{460}$) of the particles in Milli-Q H$_2$O. Briefly, five samples of ICP-N$_3$ particles in H$_2$O were prepared at varying dilutions and the absorbance at 460 nm was measured by UV-Vis. Subsequently, the iron concentration of each sample was determined by ICP-MS. Each sample was prepared in a matrix consisting of 3% HNO$_3$, 5 ppb indium (internal standard), and deionized water. The iron concentration was plotted vs. A$_{460}$, and the data was fit by a simple linear regression model. The slope of the line corresponds to E$_{460}$ of about 2870 L·mol$^{-1}$ cm$^{-1}$ arising from the LMCT of the ICP-N$_3$ particles, allowing for spectroscopic determination of iron concentration.

The weight of the particles produced by the above procedure is expected to be in the range of 10-1000 kDa, since a small portion of the as-synthesized particles pass through a 100 kDa cutoff filter. Supporting this observation, the predicted degree of polymerization for ditopic 3,4-HOPOs is approximately 1000 repeat units under the reaction conditions given above, when estimated from literature stability constants of the 3,4-HOPO-Fe(III) complex.

All DNA synthesis was carried out on a BioAutomation MM48 DNA synthesizer, according to the standard manufacturer trityl-on protocol with an additional 5 minute coupling time for non-nucleosidic phosphoramidites. Ac-dC and dmf-dG phosphoramidites were used to enable room-temperature deprotection of the nucleobases. Oligonucleotides were synthesized on 1 μmol scale and deprotected in concentrated NH$_4$OH (30%) for 17 hours at room temperature, except for poly(CCT)-Cy5-containing oligonucleotides, which were deprotected for 2 hours at room temperature. The resulting crude oligonucleotides were purified on a Varian Prostar HPLC fitted with a DynaMax Microsorb C18 Column, employing a gradient of 0-75% acetonitrile in triethylammonium acetate buffer (pH 7.0) over 45 minutes. The optical absorbance of the eluent was monitored at 254/310 nm for DBCO-containing oligonucleotides, 254/649 nm for Cy5-containing oligonucleotides, and 254/280 nm for all other oligonucleotides. DBCO-terminated oligonucleotides were lyophilized, resuspended in H$_2$O, and conjugated immediately to ICP-N3 nanoparticles. Disulfide-terminated oligonucleotides were lyophilized, reduced to the free thiol and conjugated to AuNPs as described in Hurst et al., *Anal. Chem.*, 2006, 78:8313-8318.

TABLE

| Name | Sequence | SEQ. ID. NO. | Calc. FW | Found FW |
|---|---|---|---|---|
| A-DBCO | 5'DBCO-TEG-A$_4$-AATCCTTA TCAATATTT | 1 | 6942 | 6951 |
| B-DBCO | 5'-DBCO-TEG-A$_4$-AAATATT GATAAGGATT | 2 | 7080 | 7082 |
| A-SH | 5'-HS-(CH$_2$)$_6$-A$_4$-AATCCTT ATCAATATTT | 3 | 6699 | 6689 |
| HER2-DBCO | 5'-DBCO-TEG-CTC-CAT-GGT-GCT-CAC | 4 | 5075 | 5070 |
| NONT-DBCO | 5'-DBCO-TEG-GAG-CTG-CAC-GCT-GCC-GTC-A | 5 | 6360 | 6369 |
| Cy5-DBCO | 5'-DBCO-TEG-CCTCCTCCT-Cy5-CCTCCTCCT | 6 | 6337 | 6341 |
| Cy5-SH | 5'-HS-(CH$_2$)$_6$-CCTCCTCCT-Cy5-CCTCCTCCT | 7 | 6094 | 6098 |
| Cy5-T$_{20}$-SH | 5'-Cy5-TTTTTTTTTTTTTT TTTTT-(CH$_2$)$_3$-SH | 8 | 7084 | 7084 |

Synthesis and characterization of AuNP-DNA conjugates: AuNP-SNAs synthesized in this study were prepared according to established protocols.[3] For AuNP-SNAs employed in cell uptake experiments, the number of oligonucleotides/AuNP were determined by fluorescence measurements. Oligonucleotide loading on AuNP-SNAs was quantified using a 5 nM solution of Cy5 labeled AuNP-SNAs. The Au core was dissolved using 100 mM KCN diluted in deionized water. The mixture was then incubated at room temperature for 20 minutes, and the resultant fluorescence measured against a standard curve. The standard curve consisted of the equivalent oligonucleotide sequence at a range of concentrations, dissolved in water, treated with KCN and incubated in the same manner as the SNAs. All fluorescence measurements were made using a Synergy H4 fluorescent plate reader (BioTek). Loading on the CCT-Cy5-AuNPs used as a positive control for cell uptake experiments was 113 strands/particle (CCT-Cy5-AuNP). Loading on the Cy5-T$_{20}$-AuNPs was 157 strands/particle (Cy5-T$_{20}$-AuNP). Similar values were assumed for the non-fluorescent AuNP-SNA (A-AuNP).

Synthesis of DNA-ICP conjugates: In a typical procedure, a solution was prepared containing 100 μM of the desired cyclooctyne-DNA, 0.5M NaCl, and ICP-N3 particles (500 μM in azide) in 2 mL Milli-Q H$_2$O. The resulting clear, orange solution was shaken for 16 h at 37° C. The reaction mixture was purified by ultrafiltration through an Amicon® Ultra 15 mL centrifugal filter (100 kDa MWCO), washing with 4×3 mL portions of 0.1M Tris buffer (pH 8.0), spinning at 5000 rcf for 10 minutes. The particles were resuspended in 1 mL of 0.1M Tris (pH 8.0). DNA-ICP particles remain colloidally stable at high salt concentrations (up to 1M NaCl), in contrast to the bare ICP-N3 particles, which sediment within minutes in 1M NaCl. This observation indicates a stabilizing DNA surface layer has been successfully conjugated to the particle.

Characterization of DNA-ICP conjugates: The size, charge, and DNA-loading of DNA-ICP particles were analyzed by DLS, zeta potential, and UV-Vis. The DNA concentration of a particle solution was determined by UV-Vis using the ratio ($A_{260}/A_{460}$). Bare particles in Milli-Q $H_2O$ possess $A_{260}/A_{460}$ of about 5.4. DNA-decorated particles were synthesized having a ratio $A_{260}/A_{460}$ varying from 10.9 to 15.5, indicating the presence of DNA attached to the particles. Extensive washing was conducted to ensure no free DNA remained in solution. Loading of Cy5-containing DNA was significantly lower, potentially due to the steric bulk of the dye label. Finally, the zeta potential of the bare and DNA-loaded ICPs was compared, with all samples prepared at identical dilution in 10 mM Tris buffer (pH 8.0) and 0.1M NaCl. The following data were collected for the ICP particles synthesized herein:

| ICP Particle Type | $\zeta_{avg}$ (mV) | $d_H$ (nm) | % $A_{260}$ DNA |
|---|---|---|---|
| Bare | −18.9 | 14 ± 2 | — |
| A-ICP | −35.2 | 31 ± 10 | 53% |
| B-ICP | −33.7 | 32 ± 8 | 60% |
| Her2-ICP | −31.1 | 31 ± 13 | 61% |
| NonTarget-ICP | −33.4 | 31 ± 11 | 65% |
| Cy5-ICP | −23.7 | n/a* | 14% |

Figure 6:
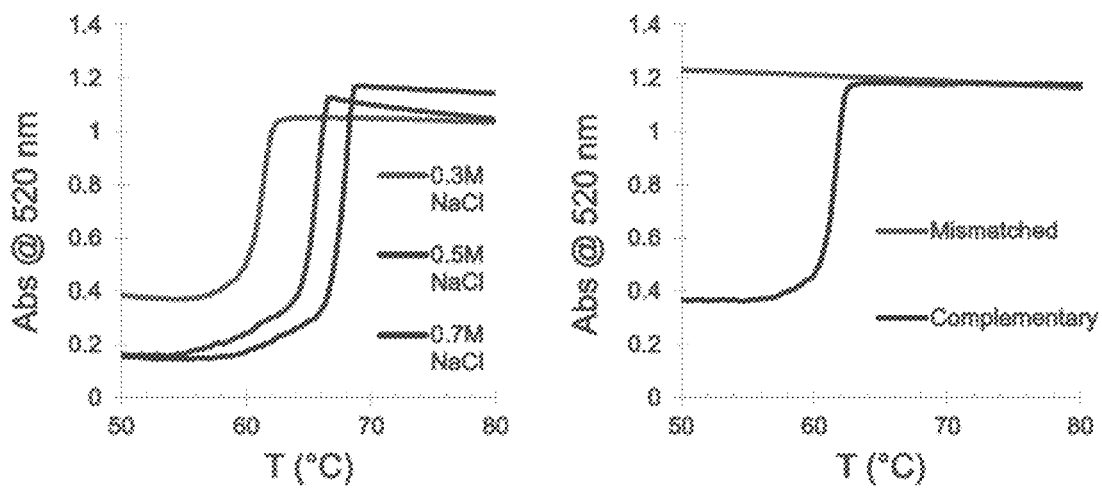
FIG. 6 shows thermal denaturation of complementary (left) and non-complementary (right) ICP/AuNP-DNA conjugates.

Thermal Denaturation Studies: DNA-ICP particles bearing complementary sequences with a 17 base-pair overlap (A-ICP) and (B-ICP) were mixed at varying salt concentrations in 0.1M Tris buffer (pH 8.0) and heated from 20° C. to 80° C. at a rate of 0.25° C. per minute. At room temperature, insoluble aggregates formed within 30-60 minutes of mixing the complementary DNA-ICPs. Upon heating, a sharp melting transition was observed, consistent with high DNA surface loading of the ICP particles. The same behavior was not observed for a pair of DNA-ICPs with mismatched sequences (B-ICP and NonTarget-ICP). The free DNA duplex has a melting temperature of 54° C. in 0.3M NaCl, compared to >60° C. for the DNA-ICPs, depending on the NaCl concentration. The same experiment was repeated using a gold nanoparticle/DNA-ICP pair (A-AuNP and B-ICP). The results are shown in FIG. 6 at increasing NaCl concentrations.

Figure 7:
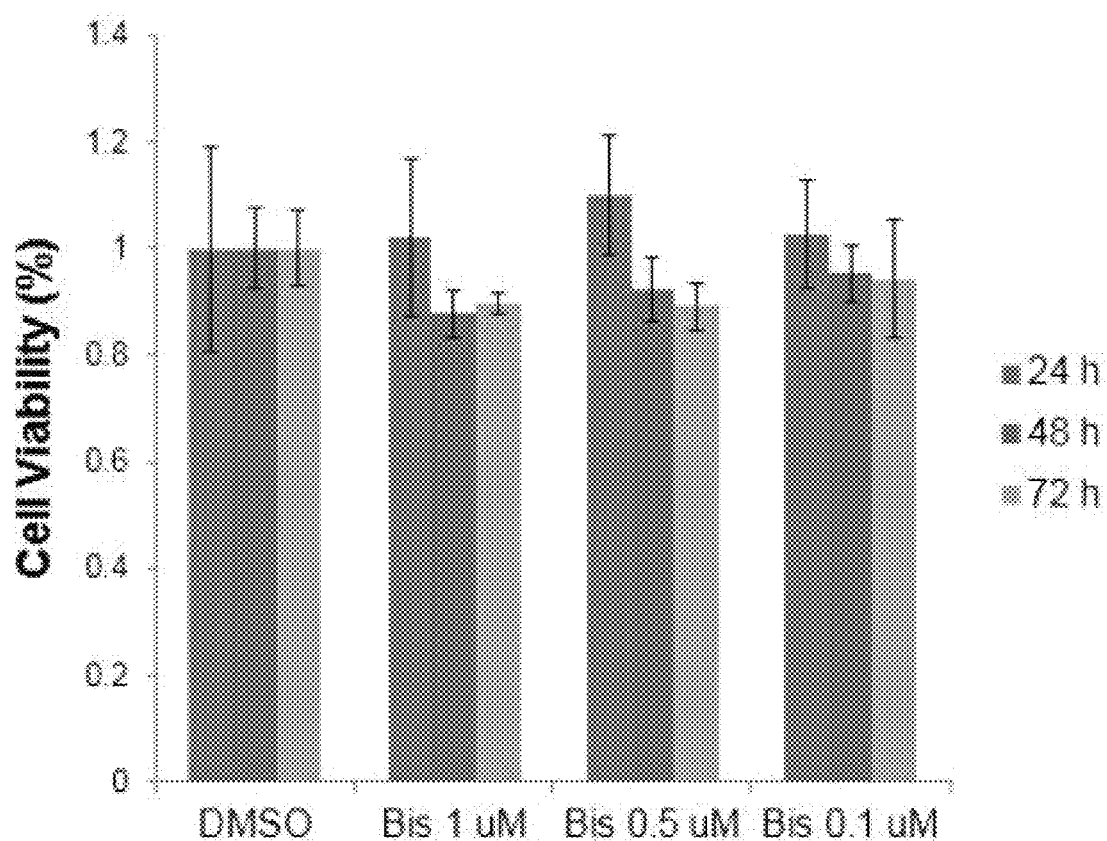
FIG. 7 shows MTT toxicity assay of parent ICP ligand 3 at various time points and concentrations.

MTT toxicity assay of DABA-BI-HP-N3 ligand: To ensure the parent ligand comprising the particle core did not exhibit cellular toxicity, an MTT assay was performed. C166 cells were seeded in a 96-well plate at a population of 5×10³ cells per well. After 24 h, the cells were treated with 0.1 mL of compound (3) (1 µM in OptiMEM) and incubated at 37° C. for 24 h. After incubation, the compound was removed from the cells and replaced with 0.1 mL of complete DMEM (supplemented with 10% fetal bovine serum and 1% penicillin/streptomycin). Cell viability was measured by MTT assay at 24 h, 48 h, and 72 h, following the addition of compound 3 to the cells. Briefly, cells were incubated with 0.1 mL of complete DMEM. 10 µL of MTT solution (5 mg/mL MTT in 1×PBS; Molecular Probes) was added into each well of cells and cells were incubated at 37° C. for 2 h. After incubation, 0.1 mL of SDS-HCl solution (0.1 g/mL SDS in 0.01 M HCl) was added to each well to solubilize the formazan product, and cells were further incubated at 37° C. overnight. After overnight incubation, the absorbance of the cell lysate was measured at 570 nm using a Synergy 114 Multimode Microplate Reader (Biotek). The relative cell viability compared to control wells containing cells treated with DMSO in OptiMEM was calculated. Reported values represent the mean±SE of three independent experiments, as shown in FIG. 7.

Cell culture uptake studies: For visualizing cell uptake by confocal microscopy, cervical cancer (HeLa) and C166 mouse endothelial cells were cultured in DMEM supplemented with 10% Fetal Bovine Serum (Atlanta Biologicals) and 1% Penicillin/streptomycin (Life Technologies).

All microscopy was performed using an SP5 laser scanning confocal microscope. Cellular images were obtained by culturing HeLa cells in supplemented Dulbecco's Modified Eagle Medium (DMEM, Life Technologies) at approximately 30% confluency in Nunc Lab-Tek II borosilicate-bottom chamber slides (Thermo Scientific). Cells were allowed to attach for 24 hours, after which they were washed once with PBS and resuspended in OptiMEM. Cells were then treated with either linear DNA, SNAs, or ICPs at a concentration of 100 nM (DNA basis). After 24 hours the cells were washed once with OptiMEM, and resuspended in DMEM containing Hoechst 33258 (Life Technologies). Equivalent methods were used for flow cytometry, however cells were not treated with Hoechst and instead were trypsinized for 3 minutes in 05% trypsin-EDTA (GIBCO), resuspended in OptiMEM, and analyzed using a Guava Easycyte 8HT (Millipore) equipped with a 633 nm laser.

For naked-eye visualization of cell uptake, MCF-7 cells were plated in 6 well plates (400,000 cells/well). After incubating the cells for 24 hours in DMEM+10% FBS containing medium, the cell media was changed to Optimem and the following concentrations of DNA-ICPs were added to individual wells: 0.0, 0.1, 0.5, 1.0, 2, and 5 µM. The particles were incubated in cells for 24 hours, after which the cells were washed thrice in PBS, cells were replenished with fresh media, and the cells were incubated for an additional 48 hours. Thereafter, cells were rigorously washed to remove any extracellular ICP particles, trypsinized, and immediately transferred to 1.5 ml eppendorf tubes containing PBS. The cells were then centrifuged at 1100 RPM for 5 minutes to form cellular pellets.

Western blot and gene knockdown analysis: SKOV3 cells were obtained from American Tissue Culture Collection (ATCC). The cells were incubated in 5% $CO_2$ at 37° C. in McCoy's 5A medium supplemented with 10% heat-inactivated FBS. Cells were cultured in 6 well cell culture plates (BD Biosciences) with 100,000 cells per well seeded 24 hours before treatment with ICPs. Medium was replaced with Opti-MEM (Life technologies) immediately prior to treatment with ICPs or Lipofectamine RNAimax (Life technologies) DNA. Lipofectamine transfection was performed according to manufacturer's instructions to deliver 25 pmole of DNA. After 12 hours, the medium was replaced with fresh media (McCoy's 5A with 10% FBS) and the cells incubated for another 48 hours. The cells were then washed three times with PBS, trypsinized and the pellet was resuspended in 100 µL of mammalian cell lysis buffer (Cell Signalling) containing protease and phosphatase inhibitor (Thermo Scientific). The whole cell lysates were then purified and collected by centrifugation and frozen at −80° C. Protein concentrations were determined using the BCA Protein Assay Kit (Pierce). Equal amounts of protein samples (25 µg) were fractionated by 4-20% precast gradient gel (Bio-Rad) and transferred to nitrocellulose membranes (Thermo Scientific). Membranes were dried overnight, rehydrated in PBS, then blocked for 1 hour at room temperature in blocking buffer (LI-COR Biosciences). Proteins were detected with rabbit primary antibodies against HER2 (1000:1) (Cell Signaling), mouse antibody against beta-tubulin (1000:1) (Thermo Scientific) and anti-rabbit or anti-mouse IgG-dye conjugated secondary antibodies (10,000:1) (LI-COR Biosciences). The fluorescence signal was recorded and quantified using the Odyssey Infrared Imaging System (LI-COR Biosciences) and quantified using Image Studio software (LI-COR Biosciences).

REFERENCES

[1] a) R. J. Macfarlane, B. Lee, M. R. Jones, N. Harris, G. C. Schatz, C. A. Mirkin, *Science* 2011, 334, 204208; b) D. Nykypanchuk, M. M. Maye, D. van der Lelie, O. Gang, *Nature* 2008, 451, 549-552.

[2] a) D. Zheng, D. S. Seferos, D. A. Giljohann, P. C. Patel, C. A. Mirkin, *Nano Lett.* 2009, 9, 3258-3261; b) D. S. Seferos, D. A. Giljohann, H. D. Hill, A. E. Prigodich, C. A. Mirkin, *J. Am. Chem. Soc.* 2007, 129, 5477; c) A. E. Prigodich, P. S. Randeria, W. E. Briley, N. J. Kim, W. L. Daniel, D. A. Giljohann, C. A. Mirkin, *Anal. Chem.* 2012, 84, 2062-2066.

[3] a) N. L. Rosi, D. A. Giljohann, C. S. Thaxton, A. K. R. Lytton-Jean, M. S. Han, C. A. Mirkin, *Science* 2006, 312, 1027-1030; b) D. A. Giljohann, D. S. Seferos, A. E. Prigodich, P. C. Patel, C. A. Mirkin, *J. Am. Chem. Soc.* 2009, 131, 2072.

[4] a) J. I. Cutler, K. Zhang, D. Zheng, E. Auyeung, A. E. Prigodich, C. A. Mirkin, *J. Am. Chem. Soc.* 2011, 133, 9254-9257; b) K. L. Young, A. W. Scott, L. Hao, S. E. Mirkin, G. Liu, C. A. Mirkin, *Nano Lett.* 2012, 12, 3867-3871.

[5] C. A. Mirkin, R. L. Letsinger, R. C. Mucic, J. J. Storhoff, *Nature* 1996, 382, 607-609.

[6] a) J. I. Cutler, D. Zheng, X. Xu, D. A. Giljohann, C. A. Mirkin, *Nano Lett.* 2010, 10, 1477-1480; b) K. Wagner, A. Kautz, M. Roder, M. Schwalbe, K. Pachmann, J. H. Clement, M. Schnabelrauch, *Appl. Organomet. Chem.* 2004, 18, 514-519.

[7] a) D. G. Thompson, A. Enright, K. Faulds, W. E. Smith, D. Graham, *Anal. Chem.* 2008, 80, 28052810; b) J. A. Dougan, C. Karlsson, W. E. Smith, D. Graham, *Nucleic Acids Res.* 2007, 35, 3668-3675; c) J. S. Lee, A. K. Lytton-Jean, S. J. Hurst, C. A. Mirkin, *Nano Lett.* 2007, 7, 2112-2115.

[8] a) Y. Li, X. Duan, L. Jing, C. Yang, R. Qiao, M. Gao, *Biomaterials* 2011, 32, 1923-1931; b) D. Z. Sun, O. Gang, *Langmuir* 2013, 29, 7038-7046.

[9] a) A. M. Rush, M. P. Thompson, E. T. Tatro, N. C. Gianneschi, *ACS Nano* 2013, 7, 1379-1387; b) M. P. Chien, M. P. Thompson, N. C. Gianneschi, *Chem. Commun.* (Cambridge, U. K) 2011, 47, 167-169; c) Z. Li, Y. Zhang, P. Fullhart, C. A. Mirkin, *Nano Lett.* 2004, 4, 1055-1058.

[10] J. I. Cutler, E. Auyeung, C. A. Mirkin, *J. Am. Chem. Soc.* 2012, 134, 1376-1391.

[11] a) A. K. Lytton-Jean, R. Langer, D. G. Anderson, *Small* 2011, 7, 1932-1937; b) A. M. Rush, D. A. Nelles, A. P. Blum, S. A. Barnhill, E. T. Tatro, G. W. Yeo, N. C. Gianneschi, *J. Am. Chem. Soc.* 2014, 136, 7615-7618.

[12] a) S. Dhar, W. L. Daniel, D. A. Giljohann, C. A. Mirkin, S. J. Lippard, *J. Am. Chem. Soc.* 2009, 131, 14652; b) X.-Q. Zhang, X. Xu, R. Lam, D. Giljohann, D. Ho, C. A. Mirkin, *ACS Nano* 2011, 5, 6962-6970.

[13] M. Wei, N. Chen, J. Li, M. Yin, L. Liang, Y. He, H. Song, C. Fan, Q. Huang, *Angew. Chem. Int. Ed.* 2012, 51, 1202-1206.

[14] a) P. C. Patel, D. A. Giljohann, W. L. Daniel, D. Zheng, A. E. Prigodich, C. A. Mirkin, *Bioconjugate Chem.* 2010, 21, 2250-2256; b) C. H. J. Choi, L. Hao, S. P. Narayan, E. Auyeung, C. A. Mirkin, *Proc. Natl. Acad. Sci. U.S.A* 2013, 110, 7625-7630.

[15] S. A. Jensen, E. S. Day, C. H. Ko, L. A. Hurley, J. P. Luciano, F. M. Kouri, T. J. Merkel, A. J. Luthi, P. C. Patel, J. I. Cutler, W. L. Daniel, A. W. Scott, M. W. Rotz, T. J. Meade, D. A. Giljohann, C. A. Mirkin, A. H. Stegh, *Sci. Transl. Med.* 2013, 5.

[16] A. M. Alkilany, C. J. Murphy, *J. Nanopart. Res.* 2010, 12, 2313-2333.

[17] a) A. M. Spokoyny, D. Kim, A. Sumrein, C. A. Mirkin, *Chem. Soc. Rev.* 2009, 38, 1218-1227; b) W. Lin, W. J. Rieter, K. M. Taylor, *Angew. Chem. Int. Ed.* 2009, 48, 650-658.

[18] a) W. J. Rieter, K. M. Pott, K. M. L. Taylor, W. Lin, *J. Am. Chem. Soc.* 2008, 130, 11584; b) P. F. Gao, L. L. Zheng, L. J. Liang, X. X. Yang, Y. F. Li, C. Z. Huang, *J. Mater. Chem. B* 2013, 1, 3202-3208.

[19] R. C. Huxford, K. E. deKrafft, W. S. Boyle, D. Liu, W. Lin, *Chem. Sci.* 2012, 3, 198-204.

[20] Z. D. Liu, R. C. Hider, *Coord. Chem. Rev.* 2002, 232, 151-171.

[21] J. Burgess, M. Rangel, *Adv. Inorg. Chem.* 2008, 60, 167-243.

[22] V. M. Nurchi, G. Crisponi, T. Pivetta, M. Donatoni, M. Remelli, *J. Inorg. Biochem.* 2008, 102, 684-692.

[23] a) G. Szigethy, K. N. Raymond, *Inorg. Chem.* 2010, 49, 6755-6765; b) S.-H. Cho, T. Gadzikwa, M. Afshari, S. T. Nguyen, J. T. Hupp, *Eur. J. Inorg. Chem.* 2007, 4863-4867; c) D. L. Caulder, C. Bruckner, R. E. Powers, S. Konig, T. N. Parac, J. A. Leary, K. N. Raymond, *J. Am. Chem. Soc.* 2001, 123, 8923-8938.

[24] R. C. Scarrow, P. E. Riley, K. Abudari, D. L. White, K. N. Raymond, *Inorg. Chem.* 1985, 24, 954-967.

[25] S. J. Hurst, A. K. R. Lytton-Jean, C. A. Mirkin, *Anal. Chem.* 2006, 78, 8313-8318.

[26] Note that the gold core is capable of quenching the fluorescence of dye-labeled oligonucleotides, which may lower the apparent fluorescence intensity.

[27] K. Zhang, L. Hao, S. J. Hurst, C. A. Mirkin, *J. Am. Chem. Soc.* 2012, 134, 16488-16491.

What is claimed is:

1. A compound having a structure

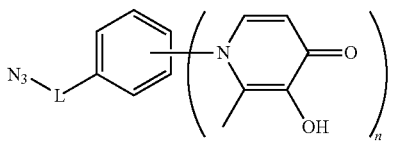

wherein

L is $C_{1-20}$alkylene or —C(O)NH—$C_{1-20}$alkylene; and n is 1 or 2.

2. The compound of claim 1, wherein n is 1.

3. The compound of claim 2, wherein the pyridone moiety is attached to the phenyl at the para position.

4. The compound of claim 1, wherein n is 2.

5. The compound of claim 4, wherein the pyridone moieties are attached to the phenyl at each meta position.

6. The compound of claim 1, wherein L is $C_{1-20}$alkylene.

7. The compound of claim 1, wherein L is —C(O)NH—$C_{1-20}$alkylene.

8. A polynucleotide comprising at a terminus a moiety comprising:

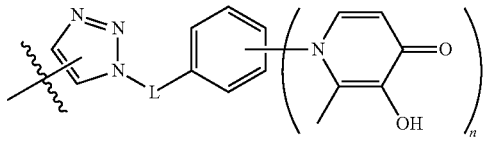

wherein

L is $C_{1-20}$alkylene or —C(O)NH—$C_{1-20}$alkylene; and n is 1 or 2.

9. The polynucleotide of claim 8, wherein n is 1.

10. The polynucleotide of claim 8, wherein n is 2, and the pyridone moieties are attached to the phenyl at each meta position.

11. The polynucleotide of claim 8, wherein the terminus of the polynucleotide has a structure:

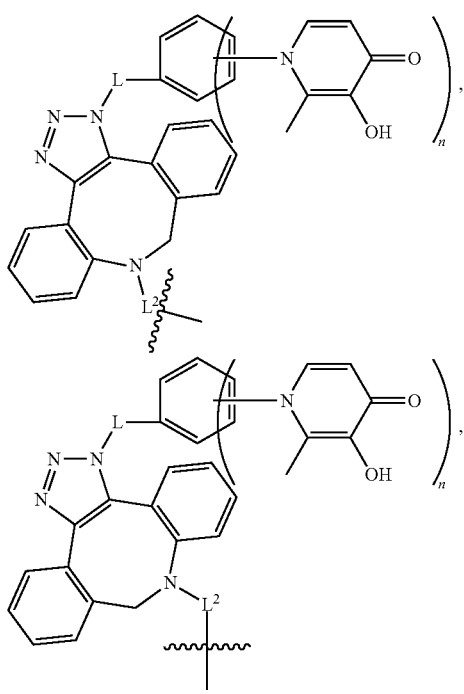

or a mixture thereof,

L² is C₁₋₁₀ alkylene, —C(O)—C₁₋₁₀ alkylene-Y—, and —C(O)—C₁₋₁₀ alkylene-Y—C₁₋₁₀ alkylene-(OCH₂CH₂)$_m$—Y—;

each Y is independently selected from the group consisting of a bond, C(O), O, NH, C(O)NH, and NHC(O); and m is 0, 1, 2, 3, 4, or 5.

12. A metal-ligand complex comprising the polynucleotide of claim 8 and Fe(III).

13. A metal-ligand complex comprising the compound of claim 1 and Fe(III).

14. The metal-ligand complex of claim 13 in the form of an infinite coordination polymer having a repeating formula of Fe₂(Compound)₃.

15. The metal-ligand complex of claim 13, further comprising a polynucleotide covalently attached via an alkyne moiety on the polynucleotide to the azide moiety on the compound to form a triazole linkage.

16. A method of inhibiting expression of a gene product encoded by a target polynucleotide comprising contacting the target polynucleotide with the metal-ligand complex of claim 15 to inhibit expression of the gene product.

* * * * *

UNITED STATES PATENT AND TRADEMARK OFFICE
CERTIFICATE OF CORRECTION

PATENT NO. : 9,617,541 B2  
APPLICATION NO. : 14/831316  
DATED : April 11, 2017  
INVENTOR(S) : Chad A. Mirkin et al.

Page 1 of 1

It is certified that error appears in the above-identified patent and that said Letters Patent is hereby corrected as shown below:

In the Specification

At Column 2, Line 51-53:  
$L^2$ is $C_{1-10}$ alkylene, $-C(O)-C_{1-10}$ alkylene$-Y-$, and $-C(O)-C_{1-10}$ alkylene$-Y-$ $C_{1-10}$ alkylene$-(OCH_2CH_2)_m-Y-$;

Should read:  
$L^2$ is selected from the group consisting of $C_{1-10}$ alkylene, $-C(O)-C_{1-10}$ alkylene$-Y-$, and $-C(O)-C_{1-10}$ alkylene$-Y-$ $C_{1-10}$ alkylene$-(OCH_2CH_2)_m-Y-$;

At Column 9, Line 28-31:  
$L^2$ can be $C_{1-10}$ alkylene, $-C(O)-C_{1-10}$ alkylene$-Y-$, and $-C(O)-C_{1-10}$ alkylene$-Y-$ $C_{1-10}$ alkylene$-(OCH_2CH_2)_m-Y-$;

Should read:  
$L^2$ can be selected from the group consisting of $C_{1-10}$ alkylene, $-C(O)-C_{1-10}$ alkylene$-Y-$, and $-C(O)-C_{1-10}$ alkylene$-Y-$ $C_{1-10}$ alkylene$-(OCH_2CH_2)_m-Y-$;

At Column 30, Line 2-4:  
$L^2$ is $C_{1-10}$ alkylene, $-C(O)-C_{1-10}$ alkylene$-Y-$, and $-C(O)-C_{1-10}$ alkylene$-Y-$ $C_{1-10}$ alkylene$-(OCH_2CH_2)_m-Y-$;

Should read:  
$L^2$ is selected from the group consisting of $C_{1-10}$ alkylene, $-C(O)-C_{1-10}$ alkylene$-Y-$, and $-C(O)-C_{1-10}$ alkylene$-Y-$ $C_{1-10}$ alkylene$-(OCH_2CH_2)_m-Y-$;

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*